(12) United States Patent
Chua et al.

(10) Patent No.: US 7,884,355 B2
(45) Date of Patent: Feb. 8, 2011

(54) POLYMER TRANSISTOR

(75) Inventors: Lay-Lay Chua, Singapore (SG); Peter Kian-Hoon Ho, Singapore (SG); Henning Sirringhaus, Cambridge (GB); Richard Henry Friend, Cambridge (GB)

(73) Assignee: Cambridge Enterprise Ltd, Cambridge (GB)

( * ) Notice: Subject to any disclaimer, the term of this patent is extended or adjusted under 35 U.S.C. 154(b) by 857 days.

(21) Appl. No.: 10/556,404

(22) PCT Filed: May 12, 2004

(86) PCT No.: PCT/GB2004/002054
§ 371 (c)(1),
(2), (4) Date: Jul. 21, 2006

(87) PCT Pub. No.: WO2004/100281
PCT Pub. Date: Nov. 18, 2004

(65) Prior Publication Data
US 2006/0284166 A1   Dec. 21, 2006

(30) Foreign Application Priority Data
May 12, 2003  (GB) ................................ 0310858.6
Apr. 16, 2004  (GB) ................................ 0408539.5

(51) Int. Cl.
*H01L 35/24* (2006.01)

(52) U.S. Cl. .......... 257/40; 257/642; 257/643; 257/759; 257/E51.005; 257/E51.007; 438/99

(58) Field of Classification Search ............ 257/40, 257/642, 643, 759, E51.005, E51.007; 438/99
See application file for complete search history.

(56) References Cited

U.S. PATENT DOCUMENTS

| 5,347,144 A | 9/1994 | Garnier et al. |
| 6,455,916 B1 * | 9/2002 | Robinson .................... 257/532 |
| 2003/0160235 A1 * | 8/2003 | Hirai ............................ 257/40 |
| 2004/0222412 A1 * | 11/2004 | Bai et al. ...................... 257/40 |

FOREIGN PATENT DOCUMENTS

| DE | 199 37 262 A1 | 3/2001 |
| WO | WO 02/065557 A1 | 8/2002 |
| WO | WO 02/067335 A1 | 8/2002 |
| WO | WO 03/041186 A2 | 5/2003 |

* cited by examiner

*Primary Examiner*—Wai-Sing Louie
(74) *Attorney, Agent, or Firm*—Sughrue Mion, PLLC

(57) ABSTRACT

A transistor including a semiconductive layer; and a gate dielectric layer comprising an insulating polymer, characterised in that the insulating polymer is crosslinked and comprises one or more units having a low cohesive-energy-density and one or more crosslinking groups and the insulating polymer includes substantially no residual —OH leaving groups.

28 Claims, 9 Drawing Sheets

BCB
based monomer

BCB
based polymer

POLYMER TRANSISTOR

The present invention concerns a new polymer transistor and a method for making the same. In particular, the present invention relates to field-effect transistors, sensors and phototransistors that operate through field-induced charge densities.

A polymer sensor is a particular type of transistor where a sensor material is in contact with the dielectric gate, the dielectric layer or the semiconductive layer, for example. The sensor responds to the presence of an analyte by selectively adsorbing it, for example, and then inducing a change in the channel conductivity through an electrostatic field effect, for example.

The polymer FET sensor comprises three terminals with the analyte solution directly contacting the thin gate dielectric to form the gate contact which gates the source-drain conductivity. The polymer FET sensor is therefore structurally distinct from the FET.

Transistors, and specifically field-effect transistors (FETs), are three-terminal devices which comprise a source contact, a drain contact, and a gate contact. A semiconductive layer bridges the source and drain contacts, and is itself spaced from the gate contact by an insulating layer called the gate dielectric. In polymer transistors, the semiconductive layer is fabricated from a semiconductive polymer, typically a n-conjugated organic polymer. This layer may be deposited in the device by a precursor route or directly by solution-processing.

A voltage is applied across the source contact and the drain contact. Further, in a field effect transistor, a voltage is applied to the gate contact. This voltage creates a field which alters the current-voltage characteristics of the semiconductive layer lying directly under the gate dielectric by causing accumulation or depletion of charge carriers there. This in turn modulates the rate at which charges pass from the source to the drain contact for a given source-drain voltage.

In the case of a phototransistor, the gate contact is transparent to light. This allows photons to pass through the gate and dielectric layer into the semiconductive layer below. The photons can generate hole-electron pairs which split and contribute to current flowing between the source and drain, thereby modulating the source-drain conductivity.

One of the greatest challenges for polymer transistors (and indeed for field-effect transistors in general) is to fabricate an ultrathin defect-free dielectric layer that also has a high-quality interface with the adjacent semiconductive layer. This dielectric layer has to show high dielectric breakdown strength, very low electrical conductivity, very low interface and bulk trapping of carriers, and good stability.

This challenge has been met for Si CMOS (Complementary Metal-Oxide-Semiconductor) FET technologies through the discovery that thermally-grown $SiO_2$ forms a nearly atomically perfect interface having very low density of interface states with the underlying Si. $SiO_2$ is robust, has high film integrity and has sufficiently high dielectric breakdown strength for practical applications. (See for example, Handbook of Semiconductor Manufacturing Technology, Y. Nishi and R. Doering Eds, Marcel Dekker N.Y. 2000, Ch 7, pp. 163-184).

For polymer transistors (particularly FET technologies), while diagnostic devices prepared on bottom-gate configuration with thermal $SiO_2$/Si substrate have shown good FET characteristics, there is a pressing need to develop alternative practical gate dielectric systems for commercial applications, such as electronic papers, printed logic circuits and radiofrequency tracking tags etc. Such gate dielectric layers must be easy to fabricate conformally on a variety of substrates in both top-gate and bottom-gate configurations. They need also to exhibit high flexure strength, significant thermal stability (including low thermal degradation rate, and high softening temperature) and environmental resistance (such as low moisture uptake).

In addition, they must be formable into a ultrathin, conformal, pinhole-free film that presents a high-quality interface with the semiconductive layer (polymer). In this regard the interface needs to be molecularly abrupt and molecularly smooth, have a low interface trap densities, and also be chemically stable.

Although there are numerous insulating polymer systems known, for example from Properties of Polymers, D. W. van Krevelen, Elsevier (Amsterdam, 1990) Ch 11, pp. 321-342, the search for a gate dielectric that can fulfill all of the above requirements is still not trivial. Furthermore, as a first step, the gate dielectric polymer must be compatible with the overall designated processing scheme of polymer FETs. For example, its formation must not destroy earlier formed layer integrities, while it itself has to survive subsequent solvent and thermal processing (if any).

Presently, several potential polymer dielectric candidates have been investigated in this regard: (1) polyimide (PI) [F. Garnier, A. Yassar, R. Hajlaoui, G. Horowitz, F. Deloffre, B. Servet, S. Ries and P. Alnot, Journal of the American Chemical Society, 115 (1993) pp.8716]; (2) poly(methyl methacrylate) (PMMA) [G. Horowitz, F. Garnier, A. Yassar, R. Hajlaoui and F. Kouki, Advanced Materials, 8 (1996) pp. 52-54]; (3) polyvinyl phenol (PVP) [H. Sirringhaus, T. Kawase, R. H. Friend, T. Shimoda, M. Inbasekaran, W. Wu and E. P. Woo, Science 290 (2000) 2123-2126] and poly (melamine-co-formaldehyde)-crosslinked PVP [M. Halik, H. Klauk, U. Zschieschang, G. Schmid, W. Radlik, S. Ponomarenko, S. Kirchmeyer and W. Weber, Journal of Applied Physics, 93 (2003) pp. 2977-2981]; (4) photoresist [G. H. Gelinck, T. C. T. Geuns and D. M. de Leeuw, Applied Physics Letters, 77 (2000) 1487-1489 and Y-M. Kim, S-W. Pyo, J-S. Kim, J-H. Shim, C-H. Suh, Y-K. Kim, Optical Materials, 21 (2002) pp. 425-428].

The polyimide system is based on thermal conversion of a precursor acid to the insoluble polyimide and is often deposited before the semiconductive polymer to give a bottom-gate configured device. The conversion requires prolonged curing at high temperatures above 200° C. with the release of water vapour (i.e. $H_2O$ leaving group) and large volume shrinkage.

The PMMA system is based on the solubility of PMMA in ester solvents (such as alkyl acetates) which do not swell or roughen the interface of the semiconductive polymer layer, which is often deposited from aromatic hydrocarbon solvents. Therefore PMMA can be deposited subsequent to the formation of the semiconductive polymer layer to give top-gate configured devices. PMMA is not a crosslinked polymer.

The PVP system is based on the solubility of PVP in alcohol and other polar solvents which again do not swell or roughen the interface of the semiconductive polymer layer. PVP however possesses acidic phenolic groups that are hygroscopic and may degrade channel properties. In particular, PVP possesses OH groups which do not have a low cohesive-energy-density. This leads to insufficiently good film-forming properties of the polymer.

The photoresist system is usually based on negative resist technology, for example, via photogenerated acid crosslinking of epoxy or oxetane groups. The crosslinked material is insolubilised and may be used in bottom- or top-gate configurations.

Unfortunately, these candidate systems often suffer from poor dielectric breakdown strength, often considerably less than 1 MV/cm. Further, they cannot be readily deposited to give ultrathin films that are conformal and pinhole-free. As a result, polymer gate dielectrics from these systems often have to be more than 300 nm thick, and they require corresponding high gate-voltage operation. In this regard, the gate voltage required to actuate the device is directly proportional to the thickness of the dielectric polymer film.

Still further, with all of these candidate systems it remains to be seen if the semiconductive polymer/dielectric interface can have sufficient chemical and thermal stability for commercial applications.

Based on electrostatic and other considerations, the optimum ratio of gate-dielectric thickness (d) to source-drain channel length (L) is between 1/10 to 1/50. For a target source-drain channel length of 2 microns or less, there is thus strong incentive to scale the gate dielectric thickness to below 100 nm. Roughly, the voltage required to operate the FET (gate voltage and drain voltage) scales linearly with d and L. Therefore, scaling down d and L together makes possible lower-voltage and faster FET operation, which is important for advantageous exploitation of the technology.

More recently a further polymer dielectric has been investigated as reported in Z. Bao, V. Kuck, J. A. Rogers and M. A. Paczkowski, Advanced Functional Materials, 12 (2002) pp. 526. The organosilsesquioxane system is based on the use of organosilsesquioxane resins as gate dielectric materials after thermal curing at elevated temperatures. Organosilsesquioxanes are low-molecular-weight —Si(R) (OH)O— materials that undergo thermal elimination of $H_2O$ to give —Si(R) $O_{1.5}$— organosilicate structures. Unfortunately, it is well known that this condensation reaction does not proceed to completion until well above 400° C., and so is not generally compatible with general organic semiconductor processing. When lower temperatures are used, the material produced is porous and hygroscopic. The residual water content is detrimental to device stability. Also the curing proceeds with huge volume shrinkage (>10%) that impacts significant stress to the underlying structures.

As for the PVP system mentioned, the organosilsesquioxane system possesses OH groups which do not have a low cohesive-energy-density. As such, the organosilsesquioxane system does not have sufficiently good film-forming properties. In particular, it is not possible to form ultrathin films with this material. Further, this material has high shrinkage during curing due to the release of water as a leaving group.

In view of the above, there still remains a need to provide further polymer dielectric systems for use in transistors. Preferably the new polymer dielectric systems will be easy to fabricate on a variety of substrates and exhibit high flexure strength and environmental resistance. Also, preferably, they will have low bulk electrical conductivity, high dielectric breakdown strength and high thermal stability. Still further they preferably will be formable into a thin, conformal, pinhole-free film that can present a high-quality interface with a semiconductive layer (polymer).

DESCRIPTION OF THE INVENTION

The present inventors have at least partially addressed the above need and, as such, in a first aspect of the present invention there is provided the use of a crosslinked insulating polymer comprising one or more structural units having a low cohesive-energy-density and one or more crosslinking groups, as a gate dielectric in a transistor.

The insulating polymer includes substantially no residual —OH leaving groups.

Further, in a second aspect of the present invention there is provided a transistor including a semiconductive layer; and a gate dielectric layer comprising an insulating polymer; characterised in that the insulating polymer is crosslinked and comprises one or more structural units having a low cohesive-energy-density and one or more crosslinking groups. The insulating polymer includes substantially no residual —OH leaving groups.

The insulating polymer as referred to above in relation to the first and second aspects of the present invention may be as defined anywhere below.

The transistor as referred to in the first aspect of the present invention or according to the second aspect of the present invention suitably may be a field-effect transistor or a phototransistor or a chemical sensor.

The transistor may have a top-gate or bottom-gate configuration.

Transfer characteristics of a transistor as referred to in the first aspect of the present invention or according to the second aspect of the present invention indicate that the charge-carrier mobility at the semiconductive/dielectric interface is comparable to that of a reference interface with hexamethyldisilazane-functionalised $SiO_2$-on-Si. Therefore good quality semiconductor/dielectric interfaces can be obtained according to the invention.

Figure 8:
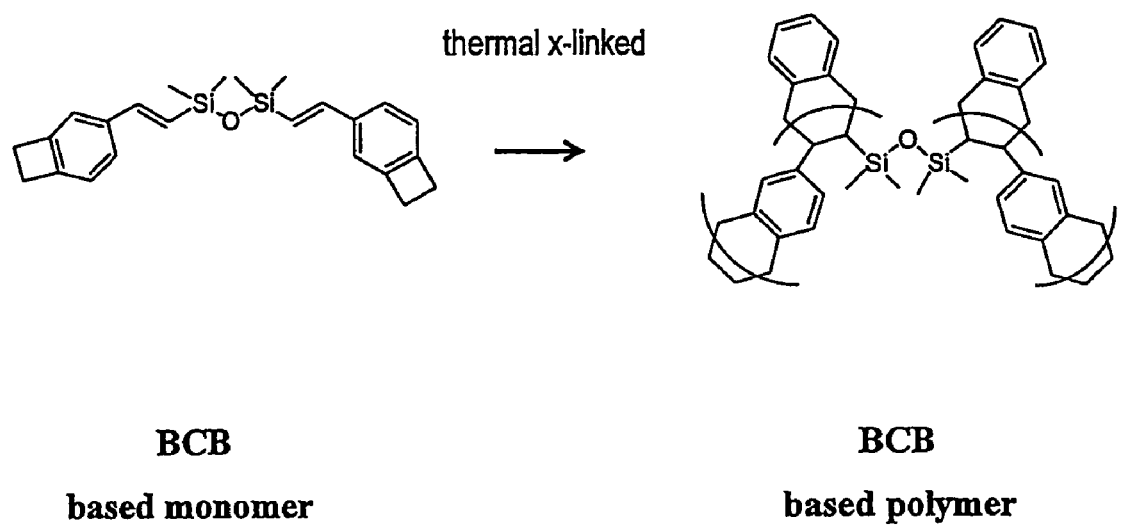
FIG. 8 illustrates an example of a gate dielectric polymer.

For example, using a poly(9,9-dioctylfluorene-co-phenylene-(N-p-isobutylphenyl)-iminophenylene) (TFB) as an exemplary polymer semiconductor, the charge-carrier mobilities obtained with the polymer shown in FIG. 8 (a BCB-based polymer) as gate dielectric have been measured to be $10^{-3}$ $cm^2/V$ s, which is similar to those obtained with $SiO_2$/Si as dielectric under given thermal processing conditions. These values are essentially limited by the semiconductive polymer itself. With other suitable semiconducting polymers, mobilities considerably higher than these can be obtained according to the present invention.

Preferably the charge-carrier mobility is as high as possible. Presently, typical values obtainable with the present invention are in the range $10^{-3}$–$10^{-1}$ $cm^2/V$ s Using the polymer shown in FIG. 8 as gate dielectric and TFB again as the test polymer, it has been possible to obtain functional FETs with the pinhole-free gate dielectric thickness (d) from 500 nm down to 50 nm. It is possible to scale further below d=50 nm. This unique ability arises from the unusually excellent film-forming properties of the insulating polymers used in the present invention. The properties can be attributed to the presence of the one or more low cohesive-energy-density structural units in the insulating polymers. In the case of the BCB-based polymer this is, in part, owing to its liquid monomer character and very low surface tension (ca. 25 dyn/cm). Therefore it is surface active.

According to the present invention, the gate leakage current density of a transistor as referred to in the first aspect of the present invention or according to the second aspect of the present invention can be less than 5 nA/mm² at a gate electric field strength of 3 MV/cm. This is similar or superior to $SiO_2$. The dielectric breakdown strength advantageously may be greater than 5 MV/cm. Both of these properties are vastly superior to those of the previously investigated dielectric polymers mentioned above.

Preferably, the gate dielectric is thermally and mechanically stable up to 150° C., more preferably up to 300° C. When this is the case, the upper shelf/operating temperature of the device becomes essentially limited by the semiconducting polymer (and the attached electrodes). For the TFB/BCB-based polymer device mentioned above, this is expected to be 180° C. This is far higher than that possible with numerous other polymer gate dielectrics. For insulating polymers in the present transistor one could use operating temperatures up to 180° C., although one typically would work in the range –20° C. to 120° C.

The thermal stability of the final crosslinked insulating polymer under anaerobic conditions (i.e. in an oxygen-free atmosphere) can be tested by the following methods:

(a) Thermogravimetric analysis. The weight loss of the polymer is plotted as a function of time at the specified temperature in vacuum or an inert gas environment. The polymer should not lose weight faster than 1%/hour at the specified temperature of 150° C.

(b) Microscopy examination. A thin film of the polymer (typically 100 nm) is made on the substrate of interest, usually on the semiconductive layer or the gate electrode layer and then observed under optical and atomic force microscopes for signs of dewetting (i.e. hole formation) as a function of temperature of the film. No defects should form within an observable field of 0.01 mm² after 1 hour at the specified temperature.

Also, it has been found that the present transistor has good saturation in the device output characteristics.

Furthermore, it has been found that curing of the present insulating polymer can be achieved by rapid thermal processing (RTP) without substantial degradation of the polymer.

Finally, the insulating polymer in the present transistor has been found to be robust, particularly with regard to processing during device manufacture. This can be attributed to the chemical and mechanical stability of crosslinking.

Without wishing to be bound by theory, it is thought that the unique properties of the one or more low cohesive-energy-density structural units substantially are responsible for the desirable device characteristics obtained with the transistor as referred to in the first aspect of the present invention or according to the second aspect of the present invention. In this regard, crosslinked polymers bearing the low cohesive-energy-density structural units (typically in combination with other suitable groups like aromatic rings, or alkyl chains) have a low surface tension, high thermal stability, high chemical and environmental stability, low bulk conductivity and high dielectric breakdown strength.

Preferably, the crosslinked insulating polymer per se has low-conductivity, preferably lower than $10^{-16}$ S/cm, and high dielectric breakdown strength, preferably higher than 0.5 MV/cm, more preferably higher than 3 MV/cm.

The crosslinked polymer will not dewet the substrate under normal processing conditions.

Dielectric breakdown strength can be tested in a standard electrode/dielectric film/electrode structure.

Preferably, the insulating polymer has a static dielectric constant of at least 2.2. More preferably the static dielectric constant is as high as possible. Reasonably the static dielectric constant will be in the range of from 2.2 to 6. This can be measured using a capacitance meter on the above electrode/dielectric film/electrode structure. (The BCB-based polymer has a static dielectric constant of 2.65).

The final crosslinked insulating polymer comprises one or more low cohesive-energy-density structural units. Cohesive energy density refers to the energy required to separate out the structural units against their van der Waals interaction. This property is extensively discussed for example in Properties of Polymers. Their Correlation with Chemical Structure: Their Numerical Estimation and Prediction from Additive Group Contributions, D. W. van Krevelen, (Elsevier, N.Y. 1990) Ch. 7 pp. 189, and Ch. 8 pp. 227.

Structural units that fall within this category will be well known to the skilled person. Preferably, the low-cohesive-energy-density structural units have a cohesive energy density of less than 300 J/cm³. More preferably, the low-cohesive-energy-density structural units have a cohesive energy density of less than 200 J/cm³. Also preferably, the low-cohesive-energy-density structural units have a cohesive energy density of greater than 100 J/cm³. Most preferably, the low-cohesive-energy-density structural units have a cohesive energy density in the range of from 100 to 200 J/cm³.

An example of a structural unit that possess such a property is a siloxane having an $Si(R)_2$—O—$Si(R)_2$, $Si(R)_2$—O—Si (R), or Si(R)—O—Si(R) group where each R independently comprises a hydrocarbon. The hydrocarbon may be saturated or unsaturated. Preferred R groups include alkyl, aryl, cycloalkyl, alkoxyl, and aryloxyl groups. A preferred alkyl group is methyl. A preferred aryl group is phenyl. In one preferred embodiment all R are methyl. In another preferred embodiment, all R are phenyl. Where R is a phenyl group, this will increase the dielectric constant of the insulating polymer and will further improve the thermomechanical properties of the insulating polymer.

R also may be selected to comprise a further siloxane moiety. This will result in the insulating material having a linear or cyclic siloxane backbone, for example as shown below:

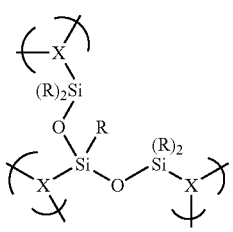

I where each X is a crosslinking group and each R is as defined above.

A further example is a fluorinated phenyl ether —$C_6F_4$—O—$C_6F_4$—. Other examples can be obtained by group-contribution estimation according to the formulae given in the book.

By way of example, $Si(CH_3)_2$—O—$Si(CH_3)_2$ has a cohesive energy density of about 150 J/cm$^3$.

Preferably, the insulating polymer comprises a plurality of low cohesive-energy-density structural units. In this regard, preferably, the content of low cohesive-energy-density structural units in the polymer is in the range of from 25 to 95% by weight.

With regard to the structure of the insulating polymer, as mentioned above, the insulating polymer includes substantially no residual —OH leaving groups. Preferably, the insulating polymer includes no residual —OH leaving groups. More preferably, the insulating polymer includes substantially no —OH groups (including residual —OH leaving groups). Most preferably, the insulating polymer includes no —OH groups. The reasoning for this can be best understood in relation to the process for forming the dielectric layer comprising the present insulating polymer. In this regard, typically, the gate dielectric layer is deposited by solution processing. Preferably, the solution contains a reactant material for making the crosslinked insulating polymer. The reactant material is cured to make the crosslinked insulating polymer. One common mechanism for curing is a condensation reaction which crosslinks the reactant material. This condensation reaction typically involves the loss of —OH leaving groups from the reactant material. However, where curing proceeds via a condensation reaction with the loss of —OH leaving groups, this typically will not remove all —OH leaving groups that were present in the reactant material. Thus, the final crosslinked insulating polymer will include residual —OH leaving groups.

Preferably, the insulating polymer does not include more than 1% by weight —OH groups. More preferably, the insulating polymer contains less than 0.1% by weight —OH groups.

If the final insulating polymer includes residual —OH groups then this indicates that —OH leaving groups were present in the reactant material. If —OH leaving groups are present in the reactant material, this imparts high surface tension which means that a solution containing the reactant material will have insufficiently good film forming properties. Further, the presence of —OH leaving groups in the reactant material typically will lead to some loss of $H_2O$ during curing. This leads to disadvantageous shrinkage of the film during curing.

As such, the reactant material for making the crosslinked insulating polymer substantially should not include any —OH leaving groups. More preferably, the reactant material does not include any —OH leaving groups. Still more preferably, the reactant material substantially does not include any —OH groups. Most preferably, the reactant material does not include any —OH groups.

A low level of —OH groups (including —OH leaving groups) can be tolerated in the reactant material. In this regard, preferably the reactant material does not include greater than 10% by weight —OH groups. If the reactant material includes 10% by weight or less of —OH groups then, after curing, the insulating polymer will include substantially no residual —OH leaving groups as required by the present invention. More preferably, the reactant material contains less than 5%, even more preferably less than 0.5% by weight —OH groups.

Preferably, the insulating polymer comprises a plurality of $Si(R)_2$—O—$Si(R)_2$, $Si(R)_2$—O—$Si(R)$ and/or $Si(R)$—O—$Si(R)$ units. In this regard, preferably, the content of $Si(R)_2$—O—$Si(R)_2$, $Si(R)_2$—O—$Si(R)$ and/or $Si(R)$—O—$Si(R)$ units in the polymer is in the range of from 25 to 95% by weight.

It is preferred that the backbone of the insulating polymer comprises one or more low cohesive-energy-density structural units. The insulating polymer may further comprise side groups comprising one or more low cohesive-energy-density structural units.

In one embodiment, one or more $Si(R)_2$—O—$Si(R)_2$, $Si(R)_2$—O—$Si(R)$ and/or $Si(R)$—O—$Si(R)$ units in the insulating polymer may be comprised in one or more side chains to the polymer backbone. In this embodiment, the backbone may be any polymer fragment that is stable at the curing temperature used to form the insulating polymer (typically at least 150° C.). Suitable polymer backbones may comprise aromatic, alkyl, and/or cycloalkyl structural units.

It is preferred that there are one or more low cohesive-energy-density structural units in the polymer backbone. This is preferred because this has been found to improve thermal stability, film forming properties, and chemical and environmental stability; and to lower electrical conductivity, and trapping of charge carriers.

Where the polymer backbone comprises a low cohesive-energy-density structural unit (preferably a repeat unit comprising a low cohesive-energy-density structural unit), the polymer backbone may include other repeat units. Examples of other possible repeat units include aromatic, alkyl, and cycloalkyl units.

Preferably, the crosslinking group in the insulating polymer is derivable from a crosslinkable group in the reactant material that can be cured without the loss of a leaving group. Suitable mechanisms under which such a crosslinkable group may be cured include an addition reaction such as the Diels-Alder reaction. An example of a system which would undergo the Diels-Alder reaction is a crosslinkable group including benzocyclobutene and alkene. An example of a further system that would undergo an addition reaction is a crosslinkable group including hydrosilane and alkene. The advantage of crosslinkable groups that can be cured without the loss of a leaving group is that problems relating to shrinkage of the film during curing are avoided.

In view of the above, it will be appreciated that it is preferred that the crosslinkable group in the reactant material for forming the present insulating polymer includes an alkene.

A preferable thermally-crosslinkable group comprises benzocyclobutene (BCB) and alkene. As such, a preferable crosslinking group in the insulating polymer comprises 2,3-disubstituted tetrahydronapthalene. Another preferred thermally-crosslinkable groups comprises s-cis-diene (such as cyclopentadiene) and alkene.

A preferred ultraviolet-crossslinkable group comprises a substituted or unsubstituted styrene.

A preferred crosslinkable group that can be crosslinked by rapid thermal anneal, with or without exposure to UV, comprises Si—H and alkene.

Referring to BCB, by appropriate substitution of the benzocyclobutene ring, the required curing (typically by rapid thermal anneal) temperature can be brought below 200° C., more specifically in the range 150° to 200° C. or even below 150° C. In this regard, reference is made to A. K. Sandra, R. K. Saini, and W. E. Billups, Chem. Rev. 103, 1593 (2003).

A preferred insulating polymer according to this invention comprises the general formula II:

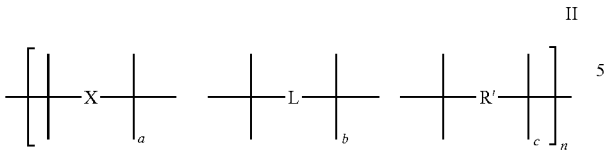

II where X is a crosslinking group, L comprises a low cohesive-energy-density structural unit and $R^1$ is a hydrocarbon, $0.01<a<0.75$, $0.25<b<0.95$, $0<c<(1-a-b)$. Where present, $R^1$ will provide further integrity and structure for the polymer chain.

A more preferred insulating polymer according to this invention comprises a repeat unit having the general formula III:

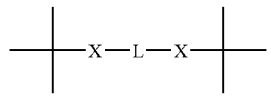

III where X and L are as defined above.

Even more preferably, the insulating polymer according to this invention comprises a repeat unit having formula IV, V or VI:

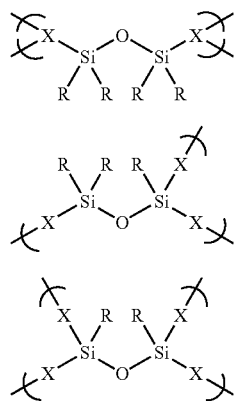

IV

V

VI where X and R are as defined above and each X may be the same or different and each R may be the same or different.

Referring to all of the general formulae I to VI above, each crosslinking group X is derived from a crosslinkable group Y. Examples of crosslinkable groups Y and their corresponding crosslinking groups X are shown below in (a) to (e):

(a) thermally-crosslinkable alkene-BCB moieties (Y):

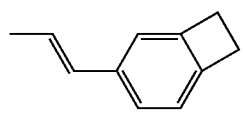

VII or the corresponding generalised substituted alkene-BCB moieties:

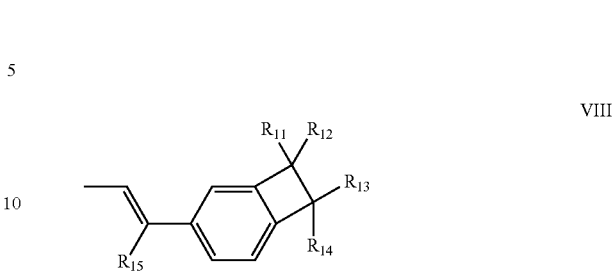

VIII where each of $R_{11\ldots15}$ is as R is defined above, preferably —H, or —$CH_3$ Such structures can be crosslinked by rapid thermal anneal. The reaction involves thermal ring-opening of benzocyclobutene to give o-quinodimethane, followed by $4\pi+2\pi$ Diels-Alder cycloaddition reaction of the resultant diene with the alkene moiety. If $R_{11\ldots14}$ are all —H, the requisite rapid thermal processing (RTP) temperature is high (about 9 seconds at 290° C., and correspondingly longer time at lower temperatures). If one or more of $R_{11\ldots14}$ is substituted by —$CH_3$ for example, the requisite RTP temperature becomes lower. If both $R_{11}$ and $R_{13}$ are —$CH_3$ for example, the RTP temperature is expected to decrease favourably to below 200° C.

At least two groups of general formula VII or VIII are needed on each monomer in order to make the crosslinked insulating material.

The final crosslinked moiety (X) present in the insulating polymer is then represented by the generalised formula IX:

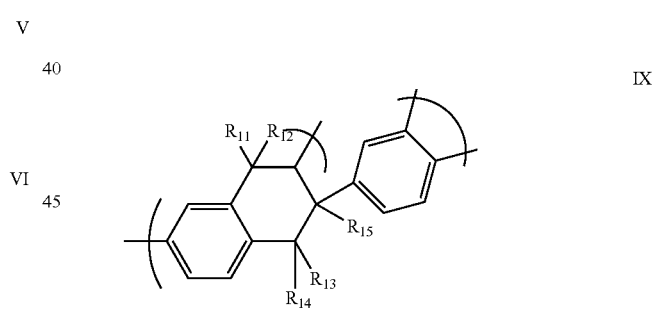

IX where $R_{11\ldots15}$ are as defined above. Referring to general formula IV, each X can comprise a group having general formula IX.

(b) thermally-crosslinkable BCB and alkene complementary moieties:

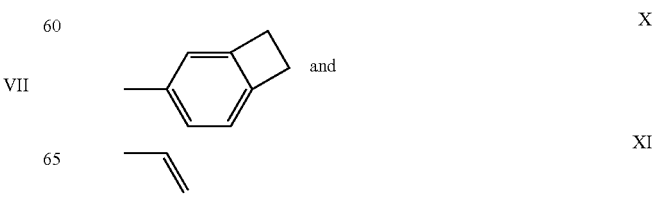

X and

XI or the corresponding generalised substituted BCB and alkene moieties:

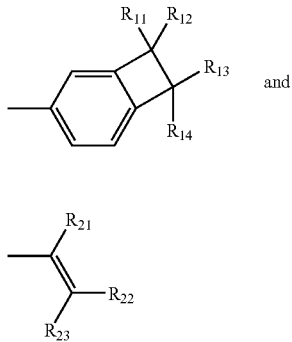

XII

XIII where each of $R_{11\ldots14}$ and $R_{21\ldots23}$ is as R is defined above, preferably $R_{11\ldots14}$=—H, —CH$_3$; and $R_{21\ldots23}$=—H, —CH$_3$ A BCB and an alkene couple together to form a crosslinking group. A crosslinkable group (Y) on a monomer in the reactant material desirably can comprise (a) one group selected from general formulae X to XIII; or (b) one group of general formula X or XII and one group of general formula XI or XIII.

At least three groups selected from general formulae X to XIII are needed on each monomer in order to make the crosslinked insulating polymer. Preferably, two groups of general formula X or XII and two groups of general formula XI or XIII are present on each monomer.

Again such structures can be crosslinked by rapid thermal anneal. The reaction involves thermal ring-opening of benzocylclobutene to give o-quinodimethane, followed by 4π+2π Diels-Alder cycloaddition reaction of the resultant diene with the alkene moiety. If $R_{11\ldots14}$ are all —H, the requisite rapid thermal processing (RTP) temperature is high (about 9 seconds at 290° C., and correspondingly longer for lower temperatures). If one or more of $R_{11\ldots14}$ is substituted by —CH$_3$ for example, the requisite RTP temperature becomes lower. If $R_{11}$ and $R_{13}$ are —CH$_3$ for example, the RTP temperature is expected to decrease favourably to below 200° C.

The final crosslinked moiety (X) present in the insulating polymer is then represented by the generalised formula XIV:

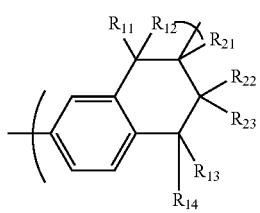

XIV where $R_{11\ldots14}$ and $R_{21\ldots23}$ are as defined above. Referring to general formulae V and VI, each X independently can comprise a group having general formula XIV.

(c) thermally-crosslinkable s-cis-diene (such as cyclopentadiene) and alkene complementary moieties:

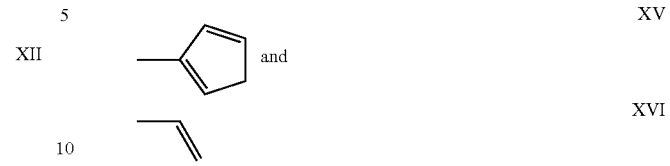

XV

XVI or the corresponding generalised substituted s-cis-diene (such as cyclopentadiene) and alkene moieties:

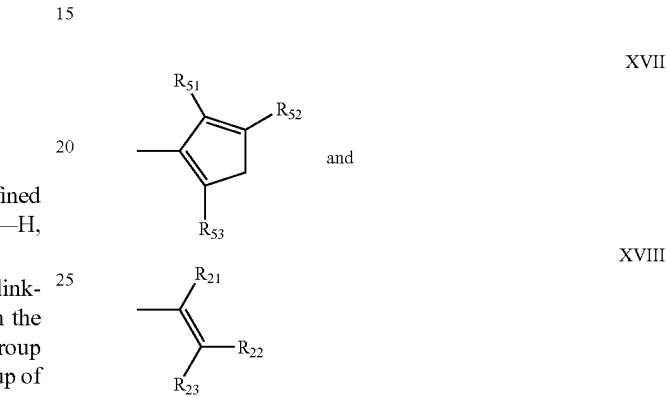

XVII

XVIII where each of $R_{51\ldots53}$ and $R_{21\ldots23}$ is as R is defined above, preferably $R_{51\ldots53}$=—H, —CH$_3$; and $R_{21\ldots23}$=—H, —CH$_3$ A s-cis-diene and an alkene couple together to form a crosslinking group. A crosslinkable group (Y) on a monomer in the reactant material desirably can comprise (a) one group selected from general formulae XV to XVIII; or (b) one group of general formula XV or XVII and one group of general formula XVI or XVIII.

At least three groups selected from general formulae XV to XVIII are needed on each monomer in order to make the crosslinked insulating polymer. Preferably, two groups of general formula XV or XVII and two groups of general formula XVI or XVIII are present on each monomer.

Again such structures can be crosslinked by rapid thermal anneal below 200° C. The reaction involves 4π+2π Diels-Alder cycloaddition reaction between the diene and the dienophile (alkene) moieties.

The final crosslinked moiety (X) present in the insulating polymer is then represented by the generalised formula:

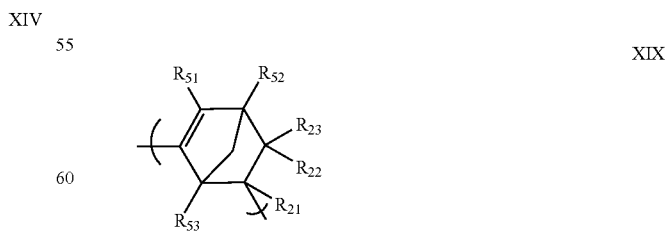

XIX where $R_{21\ldots23}$ and $R_{51\ldots53}$ are as defined above. Referring to general formulae V and VI, each X independently can comprise a group having general formula XIX.

(d) ultraviolet-crosslinkable styrenyl moieties (Y):

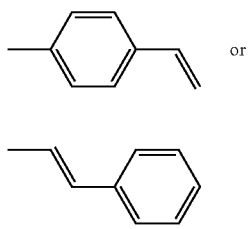

XX

XXI or the corresponding generalised substituted styrenyl moieties:

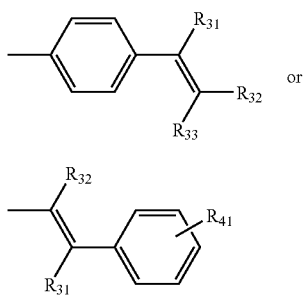

XXII

XXIII where each of $R_{31...33}$ and $R_{41}$ is as R is defined above, preferably $R_{31...33}$=—H, —CH$_3$, or -Ph; and $R_{41}$=alkyl, or aryl. At least three groups of general formula XX, XXI, XXII, or XXIII are needed on each monomer to make the crosslinked insulating material.

A crosslinkable group (Y) on a monomer in the reactant material desirably can comprise one group selected from general formulae XX to XXIII.

Such structures can be photochemically crosslinked by exposure to deep ultraviolet light at approximately 254 nm for example, with or without concurrent heating. The reaction involves photochemical ring-opening by 2π+2π Diels-Alder dimerisation of the alkene moieties. Such a system has the particular advantages in allowing for photocuring of the gate dielectric in the presence of thermally sensitive layers and also for photopatterning of the gate dielectric layer.

The final crosslinked moiety (X) present in the insulating polymer is then represented by the generalised formulae:

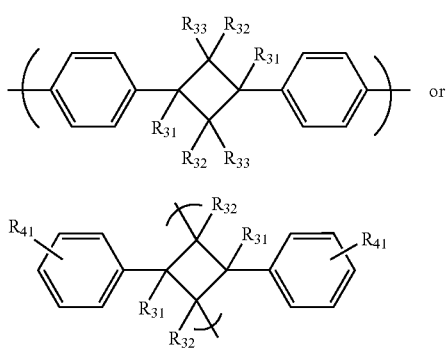

XXIV

XXV where $R_{31...33}$ and $R_{41}$ are as defined above. Referring to general formulae V and VI, each X independently can comprise a group having general formula XXIV or XXV.

(e) Si—H and alkene complementary moieties:

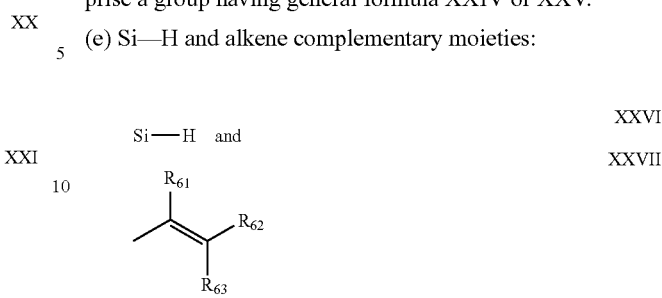

XXVI

XXVII where each of $R_{61...63}$ is as R is defined above, preferably $R_{61...63}$=—H, —CH$_3$, or -Ph A Si—H and an alkene couple together to form a crosslinking group. A crosslinkable group (Y) on a monomer in the reactant material desirably can comprise (a) one group of general formula XXVI or XXVII; or (b) one group of general formula XXVI and one group of general formula XXVII.

At least three groups of general formula XXVI or XXVII are needed on each monomer in order to make the crosslinked insulating polymer. Preferably, two groups of general formula XXVI and two groups of general formula XXVII are present on each monomer.

Such structures can be crosslinked by rapid thermal anneal (with or without deep ultraviolet exposure). The reaction involves hydrosilylation addition reaction between Si—H and the alkene moieties.

The final crosslinked moiety (X) present in the insulating polymer is then represented by the generalised formula XXVIII:

XXVIII where each of $R_{61...63}$ is as defined above. Referring to general formulae V and VI, each X independently can comprise a group having general formula XXVIII.

When considering further the structure of the present insulating polymer, it is useful to consider its method of manufacture. Principally, where the dielectric layer is formed by solution processing, a general method for making the present insulating polymer may be envisaged.

This general method comprises:

Depositing a layer of a solution containing reactant material from which the present insulating polymer is to be made;

Subjecting the deposited layer to conditions under which the reactant material is cured to form the present insulating polymer.

The reactant material substantially should not contain any —OH leaving groups as discussed above.

The reactant material may comprise monomers from which the present insulating polymer is to made, or oligomers from which the present insulating polymer is to be made, or one or more precursor polymers from which the present insulating material is to be made, or mixtures thereof.

The reactant material desirably should have a low surface tension. Preferably, the reactant material has a low surface tension, in the range of from 15 to 35 dyn/cm.

The surface tension of the monomer or oligomer or precursor polymer for the present insulating polymer can be tested by the following methods:

(a) Film-forming ability. A film of the required thickness (for example, 100 nm) is made and examined for film uniformity using profilometry, interferometry or ellipsometry, and hole defect density using optical microscope or atomic force microscope. The film uniformity expressed as a fraction of film thickness variation across a 1-inch substrate with 3-mm perimeter exclusion must be better than 2%. No defects should be found in an observation field of 0.01 mm$^2$. This is an indirect method to test the suitability of the surface tension of the material.

(b) Degree of planarisation. A 1-µm film of the monomer or oligomer or precursor polymer when coated over isolated 0.5-µm-tall isolated metal lines with linewidth less than 10-µm should give a degree of planarisation better than 90%. This is not test for surface tension per se, but one of a number of possible materials screening test.

(c) Pendant drop method. A droplet of the monomer or oligomer or precursor polymer is formed at the end of a flat-end syringe. The droplet shape is imaged by a visual system and the surface tension can be calculated using standard equations described for example in Physical chemistry of Surfaces, A. W. Adamson, (John Wiley & Sons, N.Y. 1990). The surface tension should be 15-35 dyn/cm.

Where the reactant material comprises monomers, the monomers will polymerise and crosslink when cured to form the present insulating polymer.

In this embodiment of the method, one or more of the monomers should contain the one or more low cohesive-energy-density structural units. A preferred monomer contains a low cohesive-energy-density structural unit. An even more preferred monomer further contains one or more crosslinkable groups. A most preferred monomer contains at least two crosslinkable groups.

A particularly preferred monomer has the general formula:

Y-L-Y where L comprises a low cohesive-energy-density structural unit as defined above and each Y independently is a crosslinkable group as defined above. As mentioned previously, the crosslinkable group typically comprises a hydrocarbon and preferably comprises an alkene. As also mentioned above, L preferably comprises Si(R)$_2$—O—Si(R)$_2$, Si(R)$_2$—O—Si(R), or Si(R)—O—Si(R).

As such, a preferred monomer has the formula:

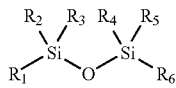

where at least two (preferably two, three or four) of R$_{1...6}$ are selected to be crosslinkable groups (Y). Preferred Y groups are as described above. The remainder of R$_{1...6}$ each independently is selected to comprise a hydrocarbon. The hydrocarbon may be saturated or unsaturated. Preferred hydrocarbon groups for R$_{1...6}$ include siloxane, alkyl, aryl, cycloalkyl, alkoxy, and aryloxy groups. Particularly preferred hydrocarbon groups for R$_{1...6}$ are methyl, phenyl and siloxane groups.

As mentioned above, a siloxane group will result in the insulating polymer having a linear or cyclic siloxane backbone.

An example of a monomer having the above general formula is shown in FIG. 8.

In the embodiment of the method as described above where the reactant material comprises monomers, the degree of crosslinking in the final insulating polymer preferably is at least 50%.

The degree of crosslinking in the final insulating polymer can be calculated as:

mass of crosslinking groups×100 mass of polymer

When the degree of crosslinking is high the insulating polymer will have a 3D crosslinked structure.

Where a solution containing oligomers is used, a layer of the solution is deposited. Following this, the layer is cured by subjecting it to conditions under which the oligomers will polymerise and crosslink to form the present insulating polymer. The solution additionally may contain monomers that polymerise and crosslink with the oligomers. One type of oligomer or more than one type of oligomer may be used in the solution. One suitable oligomer may contain one or more low cohesive-energy-density structural units, optionally in combination with one or more crosslinkable groups. A preferred oligomer contains an oligo Si(R)$_2$—O—Si(R)$_2$, Si(R)$_2$—O—Si(R), or Si(R)—O—Si(R) as defined above.

Where a solution containing one or more different precursor polymers is used, a layer of the solution is deposited. Following this, the layer is cured by subjecting it to conditions under which the precursor polymer(s) will crosslink to form the present insulating polymer. In one embodiment, suitably, the solution will contain a first and a second precursor polymer, where the second polymer is different from the first polymer.

In this embodiment, both the first precursor polymer and the second precursor polymer will comprise one or more crosslinkable groups. The first precursor polymer and/or the second precursor polymer optionally further will include one or more low cohesive-energy-density structural units.

The first precursor polymer and/or the second precursor polymer preferably comprises a poly (Si(R)$_2$—O—Si(R)$_2$), Si(R)$_2$—O—Si(R), or Si(R)—O—Si(R) homopolymer or copolymer where Si(R)$_2$—O—Si(R)$_2$, Si(R)$_2$—O—Si(R), or Si(R)—O—Si(R) is as defined above. For example, the first polymer may be a homo-poly(siloxane) with crosslinkable side chains and/or end groups, such as vinyl side chains or end groups. Further, the first polymer may be a homo-poly(siloxane) such as a poly(dimethylsiloxane) and the second polymer may be a poly(methylhydrosilane) copolymer. This will provide an insulating polymer comprising crosslinked PDMS (polydimethylsiloxane).

In the method where a solution containing one or more different precursor polymers is used, the degree of crosslinking in the final insulating polymer preferably is at least 1%, more preferably in the range 1 to 50%, even more preferably in the range 1 to 20%.

Examples of further precursors to a polysiloxane insulating polymer according to the present invention include divinyl-terminated poly(dimethylsiloxane) and poly(dimethylsiloxane-co-methylhydrosiloxane).

In the present method as described in any embodiment above, advantageously, the solvent may be a saturated hydrocarbon solvent (including hexane, cyclohexane, octane, decane, dodecane). Generally, good quality films can be obtained from such solvents. This allows the deposition to be compatible with a very wide range of organic semiconductors (which do not dissolve or swell in saturated hydrocarbon solvents). Therefore the insulating polymer, such as the BCB-based polymer shown in FIG. 8, can be deposited as the dielectric in both top-gate and bottom-gate configurations without damaging the semiconductor layer.

In the present invention, the insulating polymer must be crosslinked to the extent that it is rendered insoluble and, thus, useable in a transistor as referred to in relation to the first aspect of the present invention or according to the second aspect of the present invention. Generally, the insulating polymer will be crosslinked to the extent that it is rendered insoluble in saturated hydrocarbon solvents. Preferably, the present insulating polymer is about 1-90% crosslinked. However, the precise extent of crosslinking required will vary according to the polymer.

The thickness of the gate dielectric layer advantageously may be below 400 nm, preferably in the range 400 to 10 nm, 400 to 30 nm, more preferably 100 to 30 nm, or 100 to 10 nm depending on the source-drain channel length. In this regard, generally, design rules suggest that the gate dielectric thickness should be $1/10$-$1/50$ of the channel length. It will be appreciated that these gate dielectric thicknesses are small as compared with previously known transistors.

It has been found advantageously that a BCB-based polymer can be fabricated practically pinhole-free down to a thickness of about 10 nm.

As a consequence of an advantageously thin gate dielectric layer, the operational voltage of the transistor is correspondingly reduced. As such, the operational voltage of the transistor as referred to in the first aspect of the present invention or according to the second aspect of the present invention is preferably in the range 30 to less than 5 volts, more preferably in the range 20 to less than 5 volts, most preferably less than 5 volts.

Preferably, the semiconductive layer comprises a semiconductive polymer. However, it may comprise a semiconductive oligomer or small molecule such as a crystal/amorphous molecular organic semiconductor.

Where the semiconductive layer comprises a semiconductive polymer, an example of a suitable semiconductive polymer is a polymer comprising fluorene and/or triarylamine repeat units. However, broadly speaking, any semiconductive polymer that is partially, substantially, or even fully conjugated is preferred. Such a polymer comprising aryl-containing repeat units is further preferred. The polymer may be amorphous or more preferably semicrystalline or liquid crystalline. A preferred polymer is poly[(9,9-dioctylfluorene-2,7-diyl)-alt-(phenylene-(N-(p-2-butylphenyl)imino-phenylene)](TFB). This is a p-channel semiconductor.

In certain embodiments, it may be preferable for the semiconductive layer to be a crosslinked semiconductive polymer. This is preferred if the semiconductive layer is deposited before the gate dielectric layer and the gate dielectric is to be deposited from a solvent that would otherwise dissolve the first formed semiconductive layer. Additionally, this is preferred if the semiconductive layer is to be subjected to a subsequent solvent process that could destroy the semiconductor layer, for example; subsequent photoresist lithography.

Preferably, for top-gate-and-bottom-source-drain or bottom-gate-and-top-source-drain configurations, the semiconductive layer has a thickness less than $1/30$ of the channel length more preferably, less than $1/60$ of the channel length. For top-gate-and-top-source-drain or bottom-gate-and-bottom-source-drain configurations, the semiconductive layer has a thickness in the range of 300 nm to 10 nm, more preferably, 100 nm to 10 nm.

The present invention further provides an electronic paper, a logic circuit, such as printed logic circuit, and an RF tag including a transistor according to the first aspect of the present invention.

According to a third aspect of the present invention, there is further provided a method for making a transistor as defined above in relation to the second aspect of the present invention.

Some preferred features of the method according to the third aspect of the present invention have been described above in relation to the first and second aspects of the present invention. Further features will be described below.

The semiconductive layer forms an interface with the gate dielectric layer. Advantageously, it has been found that in the present method the interface between the semiconductive layer (typically a polymer) and the insulative polymer can be molecularly abrupt and molecularly smooth.

As mentioned above in relation to the first and second aspects of the present invention, the present transistor may have a top-gate or a bottom-gate configuration. Where the transistor has a top-gate configuration, the semiconductive material (polymer) is deposited as a layer, and optionally crosslinked, before the insulating polymer is deposited. In the bottom-gate configuration, the solution containing the reactant material is deposited and the final crosslinked insulating polymer is formed before the semiconductive layer is deposited.

The solution containing the reactant material has been described above in relation to the first and second aspects of the present invention. Further, curing the solution containing the reactant material also has been described above in relation to the first and second aspects of the present invention. Further preferred features of the solution and curing the reactant material will be described below.

In the method according to the third aspect of the present invention for making the transistor, a layer of the insulating polymer is formed on the semiconductive layer (polymer) or visa versa.

It is preferred that the insulating polymer or a precursor thereof is formed on the semiconductive layer (polymer).

Where a solution containing reactant material for making the present polymer is used, deposition of the solution may be by solution processing.

Where reactant material for making the insulating polymer is deposited by solution processing, suitable solvents will be known to those skilled in the art. Any suitable solvent that does not dissolve the underlying layer may be used. These include ester solvents, such as butyl acetate and hexyl acetate; ether solvents, such as trimethoxypropane; alcohol solvents, such as isopropyl alcohol, and propyleneglycol monomethyl ether; and saturated hydrocarbon solvents, such as dodecane, decane, isooctane, and hexane.

Generally, the solution will contain the reactant material at a concentration in the range of from 150 mg/mL to 10 mg/mL when spin-coating is used, and correspondingly less when inkjet deposition is used.

Optimum conditions for solution processing can be determined by a person skilled in this art by spin trials. Nevertheless, as guidance for obtaining a desired thickness, the present inventors have determined that the BCB based monomer shown in FIG. 8 dissolved in decane (or other hydrocarbon solvent) at a concentration of 6.3 weight/vol % in decane when spun at 2000 rpm gives a thickness of 50 nm, at 8000 rpm gives 25 nm. At 12 w/v % in decane, a spin speed of 2000 rpm gives 150 nm and 8000 rpm gives 75 nm. Alternatively, the BCB based monomer may be accurately metered in the solvent at an appropriate concentration between 1 and 50 weight/vol % by inkjet printing.

The film typically is a viscous liquid as deposited. Further, this film typically is stable at least over a few days and sometimes indefinitely even down to 30 nm in thickness.

After deposition, the deposited film is cured to form the final insulating polymer.

This curing will comprise crosslinking the reactant material. Further, in one embodiment, this curing may comprise simultaneous polymerising and crosslinking. This may be, for example, where the reactant material comprises monomers and/or oligomers.

In another embodiment, where the reactant material comprises one or more different precursor polymers, this curing may include a further step of converting a precursor polymer. Generally, the converting step will be before the crosslinking step. However, not all precursor polymers will require a converting step to form the present insulating polymer. For example, as in the case of crosslinked PDMS as mentioned above, the insulating polymer may be formed from the one or ore different precursors polymers simply by crosslinking.

The reactant material preferably should crosslink by photo or thermal curing without loss of a leaving molecule such as $H_2O$. Therefore there should be crosslinkable groups in the reactant material that crosslink by addition-type (as opposed to condensation-type) reactions. Examples of such reactions include those described above including a thermal-induced cycloaddition Diels-Alder reaction, such as the reaction between benzocyclobutene and a dienophile (the reaction exemplified in the present application), and a hydrosilylation reaction between Si—H and an alkene.

Suitably, curing in relation to any embodiment of the present method may be done by, exposure to UV, slow thermal processing or, preferably, by rapid thermal processing (RTP) or by laser anneal. The curing proceeds with very little volume change (preferably less than 5%) and so does not impart stress on the underlying structures. Also, no gases are evolved. This is particularly where the crosslinkable groups in the reactant material are cured without the loss of a leaving group.

Rapid thermal processing (RTP), sometimes also known as rapid thermal annealing (RTA), in the context of inorganic semiconductor device manufacturing is well known and is described for example in Handbook of Semiconductor Manufacturing Technology, Y. Nishi and R. Doering Eds, Marcel Dekker N.Y. 2000, Ch 9, pp. 201. RTA involves the rapid heating of the substrate to the desired temperature and holding it there for short periods of time for the desired reaction or process to take place. This can be achieved using hotplate, special rapid-thermal ovens, or radiation heating devices for example. In the above context, the desired reaction or process is often to anneal out semiconductor defects without causing dopant diffusion in the rest of the structure or to grow thin thermal oxides.

In the present method RTP may be used to cure the present insulating polymer without causing thermal damage to the rest of the organic semiconductor structure. For this application, RTP refers to rapid heating to the desired temperature (for example at a rate faster than 50° C./second) and holding it there for short periods of time (for example less than 1 min) and then rapidly quenching back to room temperature (for example at a rate faster than 50° C./second). This can be achieved by placing the substrate onto the hotplate set at the desired temperature, and then removing the substrate to a cool metal surface. Organic semiconductors have generally lower stability than inorganic semiconductors and are susceptible to undesirable irreversible changes when annealed for long periods above a threshold temperature that is characteristic of each material.

For example, the TFB polymer cannot withstand prolonged annealing for more than a few minutes above 250° C. without losing its hole-carrier mobility. RTA is a way to overcome this limitation. The present insulating polymer (for example the BCB-based polymer shown in FIG. 8) can be cured for example, at 290° C. for 10 seconds. This processing condition does not significantly degrade the hole mobility of an underlying TFB layer and allows the present insulating polymer to be used as the top-gate dielectric. For example, for the BCB-based polymer shown in FIG. 8, RTP can be achieved in 12 min at 230° C., and 8 seconds at 290° C. This minimises thermal damage to the other device structures, especially the semiconductor polymer layer.

As previously mentioned, the curing temperature of reactant material with crosslinkable groups containing BCB can be lowered by appropriate substitution of the benzocyclobutene ring.

The optimum conditions for curing depend on the thermal stability of the semiconducting layer (in the top gate configuration) and other formed structures, and can be easily determined by anyone skilled in the art using test structures and infrared spectrometry. Preferably, the reactant material is cured at a temperature of at least 150° C. to form the present insulating polymer. Also preferably, the reactant material is cured at a temperature of below 350° C. Suitable cure conditions for films 200 nm or less in thickness include 25 h at 170° C. (slow), or 3 h at 200° C., or 12 min at 230° C. or 8 s at 290° C. (RTA). The temperature specified is for the hotplate on which the article is to be placed. Alternative methods to cure include rapid thermal cycle ovens.

Typically, an inert atmosphere such as a nitrogen atmosphere with oxygen present at a level of less than 5 ppm is used during the thermal curing.

Deposition of the semiconductive material (typically a polymer) layer may be by solution processing and optionally by a precursor route. Generally, the solution will contain the semiconductive material (typically a polymer) or a precursor thereof at a concentration in the range of from 25 mg/mL to 5 mg/mL, preferably from 20 mg/mL to 10 mg/mL.

The optimum conditions for solution processing of the semiconductive material are dependent on the nature of the material. However, often a semiconductive polymer can be deposited from a 10 mg/mL to 30 mg/mL solution in an appropriate aromatic hydrocarbon (such as toluene, xylene, durene, mesitylene, tetrahydronaphthalene, chlorobenzene) or other solvents (cyclohexanone, tetrahydrofuran, chloroform, trichloroethane), by spin-casting at 1000 rpm to 8000 rpm. Alternatively, the semiconductive polymer can be dropcast or inkjet printed from these solutions at an appropriate concentration.

For top-gate configuration, the top gate electrode is deposited (for example by solution processing) after curing the gate dielectric film. The top gate electrode can be, for example, a conductive polymer complex such as p-doped poly(3,4-ethylenedioxythiophene)-poly(styrenesulphonate) (PEDT:PSS). The solution of PEDT:PSS suitably may be deposited by inkjet printing or other solution processing method, dried in air at 80-120° C. for 10 s to 10 min (preferably, 85° C., 20 s), and then reaction-bonded to the gate dielectric film by baking at 160° C.-200° C. for 1-5 min (preferably, 160° C., 2 min) under nitrogen or other inert atmosphere.

A surfactant ion-exchanged PEDT:PSSR (R long chain surfactant cation) has been found to have improved spreading on the gate dielectric film. In one particular method, the PEDT: PSSR may be made using the commercial PEDT:PSSH solution ("Baytron P™" from HC Starck of Leverkusen, Germany) with a PSS/PEDT ratio (r) of 5-6 was enriched with PSSH to 10-16. The H⁺ was then exchanged with hexadecyltrimethylammonium $CH_3(CH_2)_{15}N(CH_3)_3^+$ by precipitation with 10% excess hexadecyltrimethylammonium bromide followed by dialysis against 30% isopropanol in water. The exchange was 99% complete according to pH and FTIR analysis. The resultant PEDT:PSSR (R=$C_{16}NMe_3^+$ here) is markedly less acidic than the starting PEDT:PSSH and shows better wetting on the gate dielectric film (e.g. the BCB-based polymer according to this invention). PEDT:PSSR also does not cause undesirable doping of the channel across the ultrathin gate dielectric and is less brittle because of the long chain surfactant ion. This makes PEDT:PSSR particularly suitable for some plastic electronic applications.

Advantageously, PEDT:PSS may be thermally bonded onto the surface of the gate dielectric film without using oxygen plasma or another aggressive surface treatment that could cause damage to the dielectric layer. By way of example, PEDT:PSSR can be bonded to the surface of the gate dielectric film (for example to the surface of the BCB-based polymer) by briefly annealing at 180° C. (two minutes $N_2$). By this process, an overlayer is chemically bonded onto the surface which cannot be removed by washing in water.

Various PSS layers may be deposited on the gate dielectric film in the present transistor.

Where the semiconductive layer comprises a semiconductive polymer that is deposited before the gate dielectric layer, the semiconductive polymer should be converted (if deposited in its precursor form) and crosslinked (where desirable) before deposition of the dielectric layer over the semiconductive polymer.

Preferably, where the device is in top-gate configuration, a top-gate electrode comprising PEDT:PSS is deposited on the dielectric layer.

Where the gate dielectric layer is deposited before the semiconductive layer, the final crosslinked insulating polymer should be formed before deposition of the semiconductive layer.

Possible substrates onto which the semiconductive layer is deposited (if this is deposited first), or the dielectric layer (if this is deposited first) include glass, or plastic films including polyimide, polycarbonate, polyester and cellulose films.

If the layer that is deposited first (semiconductive or dielectric) is deposited as a precursor, this should be cured to the desired polymer before the next layer is added.

If the layer that is deposited first is to be crosslinked, this should be done before the next layer is deposited. Generally, more than one layer may not be cured simultaneously.

Furthermore, generally, conversion of a precursor polymer (where necessary) and curing of the polymer are not carried out simultaneously.

EXAMPLES

Example 1

A substrate bearing prepatterned gold source and drain electrodes. The electrodes are 20-nm thick. Channel length is 3 micron. Channel width is 10 mm. These electrode structures can be prefabricated by a host of methods including photolithography, electron-beam lithography, contact printing or inkjet printing.

The substrate is then cleaned by oxygen plasma (pressure of oxygen, 450 mbar; power 200 W; time, 10 min) in a barrier-type Plasmaline etcher, followed by Millipore water, then isopropanol rinse, and nitrogen blow-off. Hexamethyldisilazane is spun onto the substrate at 900 rpm, 30 s, and then the substrate is baked in air on a hotplate for 2 min at 120° C.

TFB (from Cambridge Display Technology, Cambridge, U.K.) at a concentration of 2.7 weight/vol % in mesitylene is spun onto the substrate at 3500 rpm, 60 s, to give a 70 nm film.

BCB based monomer (from Dow Chemical Company, MI, U.S.A.) as shown in FIG. 8 is extracted from the commercial solution and redissolved into decane at a concentration of 6.4 weight/vol %. This is spun onto the TFB film at 2000 rpm, 60 s, to give a 50 nm film. This gives a d/L ratio of 1/60. The substrate is then baked under nitrogen on a hotplate for 9 s at 290° C.

PEDT:PSS (from Cambridge Display Technology, Cambridge, U.K.) modified in-house by C16-alkylammonium surfactant ion exchange is used at a concentration of 1 weight/vol % in water, and 1-5 microlitre is drop cast onto the channel region using micropipette to define the gate electrode. The droplet is dried on a hotplate in air for 20 s at 85° C. Then the substrate is baked under nitrogen on a hotplate for 2 min at 160° C. The device is now complete and ready for evaluation.

Figure 1:
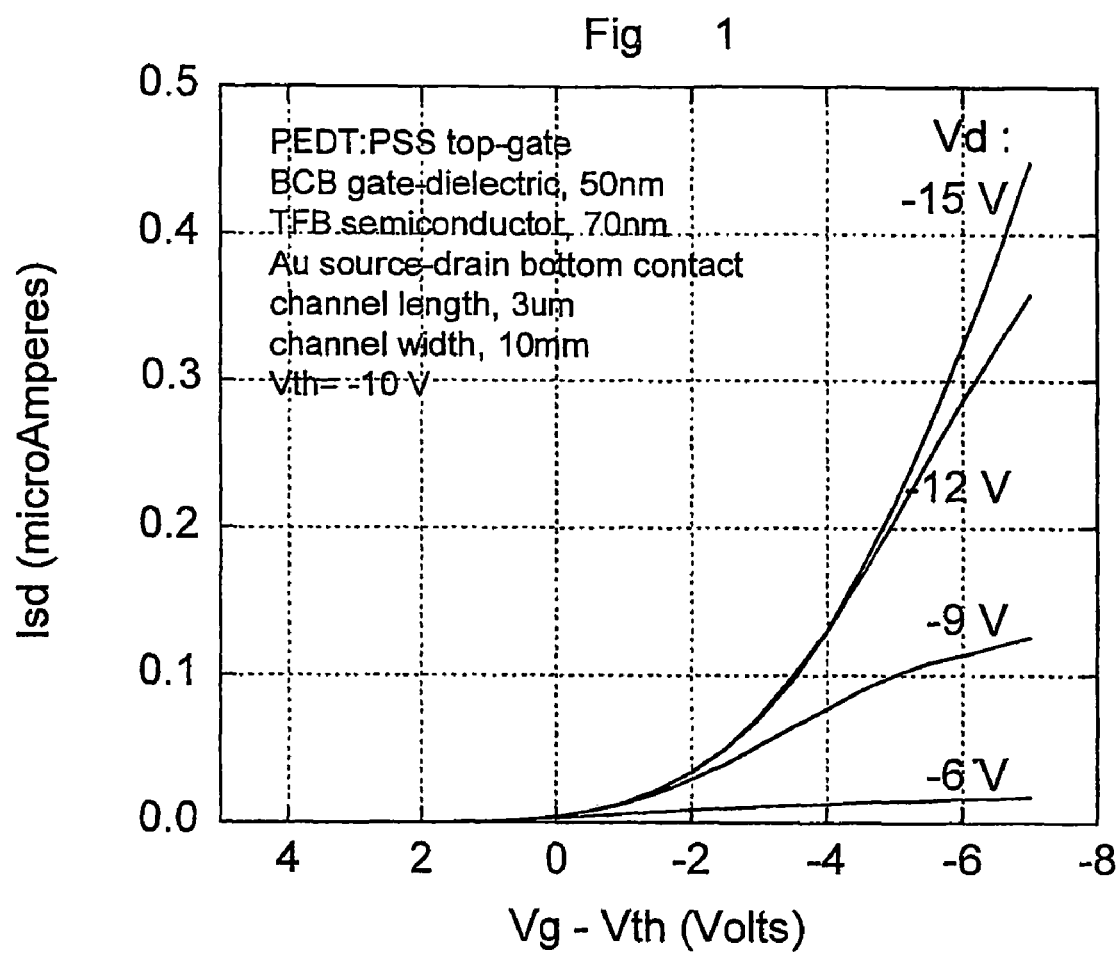
FIG. 1 illustrates the transfer characteristics for a device in accordance with a first embodiment of the invention.
Figure 2:
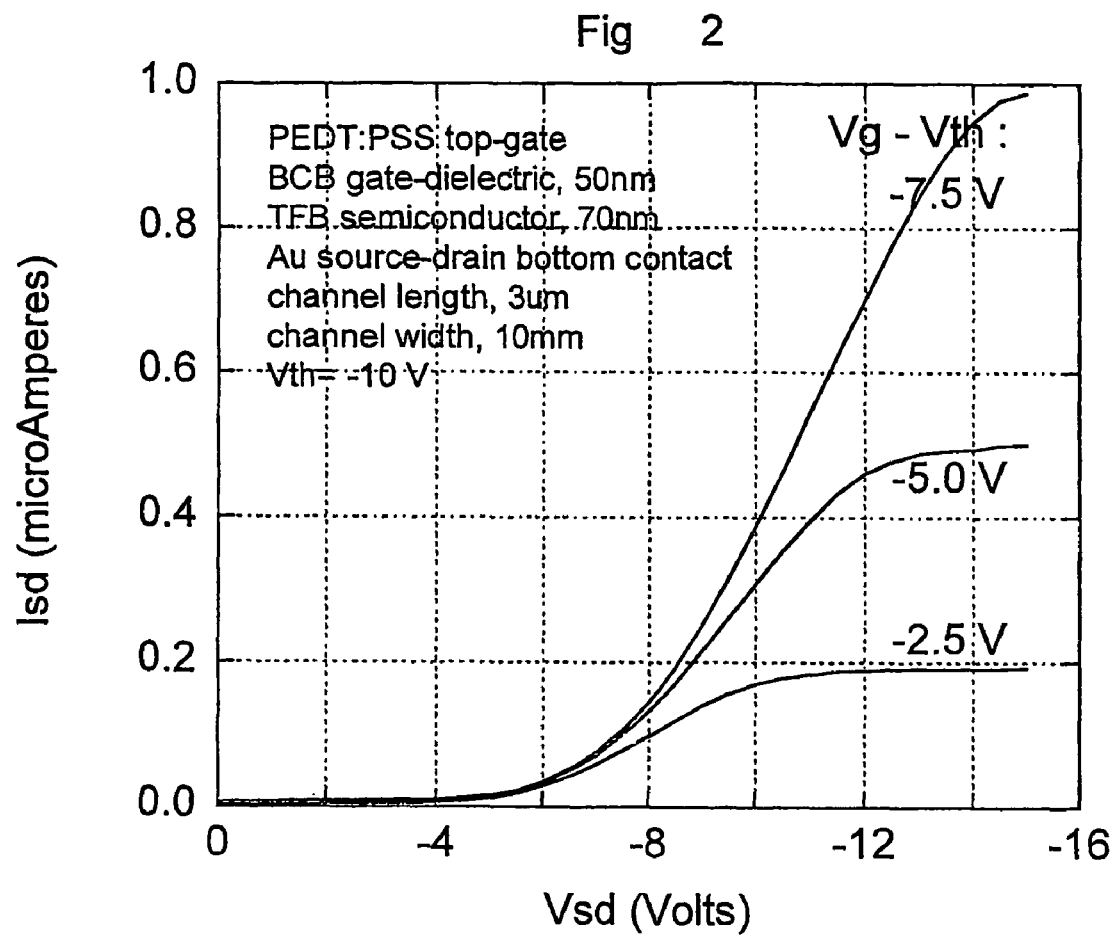
FIG. 2 illustrates the output characteristics for said device in accordance with said first embodiment of the invention.
Figure 3:
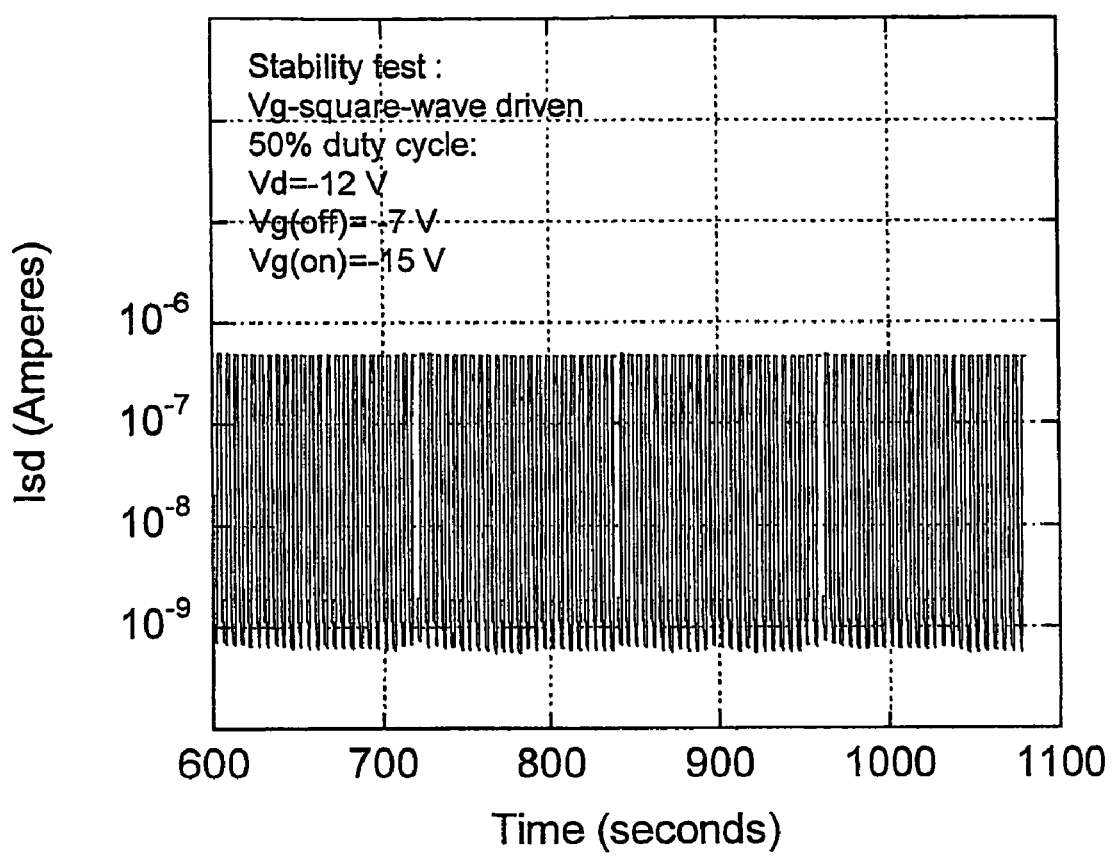
FIG. 3 illustrates the results of a stability test for said device in accordance with said first embodiment of the invention.

The transfer characteristics of this 50-nm gate dielectric device are given in FIG. 1. The threshold gate voltage ($V_{th}$) is ca. 10 volts. This is largely limited by traces of ionic impurities in the TFB semiconductor which accumulates to the interface, as evidenced by similar behaviour on separate $SiO_2$/Si bottom gate devices. A strong turn-on of the channel conductivity is found when the gate voltage ($V_g$) is increased a few volts above this threshold. An "on" source-drain channel current ($I_{sd}$) of few microAmperes is obtained for a drain voltage ($V_d$) of −12 volts, and a ($V_g$−$V_{th}$) of −7 volts. On-off ratio is better than 1000. The measured gate current leakage ($I_g$) is less than 5 nA, which is remarkably small, considering that the electric field strength in the BCB-based polymer gate dielectric at this point is ca. 3 MV/cm. The FET mobility extracted by traditional equations from the $I_{sd}$−$V_g$ slope in the linear regime is near $10^{-3}$ cm²/V s. This is comparable to best values obtained on traditional bottom-gate $SiO_2$/Si gate. The output characteristics are shown in FIG. 2. Good saturation behaviour of $I_{sd}$ is found, indicating that the device is relatively well behaved. The $I_{sd}$ value can be repeatedly cycled between the off state and the on state, as shown in FIG. 3. There is a small reversible drift associated with trace ionic impurities in the TFB. Otherwise, the TFB/BCB-based polymer interface appears remarkably stable.

Example 2

A substrate bearing prepatterned gold source and drain electrodes. The electrodes are 20-nm thick. Channel length is 3 micron. Channel width is 20 mm. The substrate is cleaned by oxygen plasma as described in Example 1. Hexamethyldisilazane is spin onto the substrate at 900 rpm, 30 s, and then the substrate is baked in air on a hotplate for 2 min at 120° C.

TFB (from Cambridge Display Technology, Cambridge, U.K.) at a concentration of 2.7 weight/vol % in mesitylene is spun onto the substrate at 3500 rpm, 60 s, to give a 70 nm film.

BCB-based monomer as shown in FIG. 8 (from Dow Chemical Company, MI, U.S.A.) is extracted and then redissolved into decane at a concentration of 6.4 weight/vol %. This is spun onto the TFB film at 6000 rpm, 60 s, to give a 150 nm film. This gives a d/L ratio of 1/20. The substrate is then baked under nitrogen on a hotplate for 9 s at 290° C.

PEDT:PSS (from Cambridge Display Technology, Cambridge, U.K.) modified in-house by C16-alkylammonium surfactant ion exchange is applied to give the top-gate electrode as described in Example 1.

Figure 4:
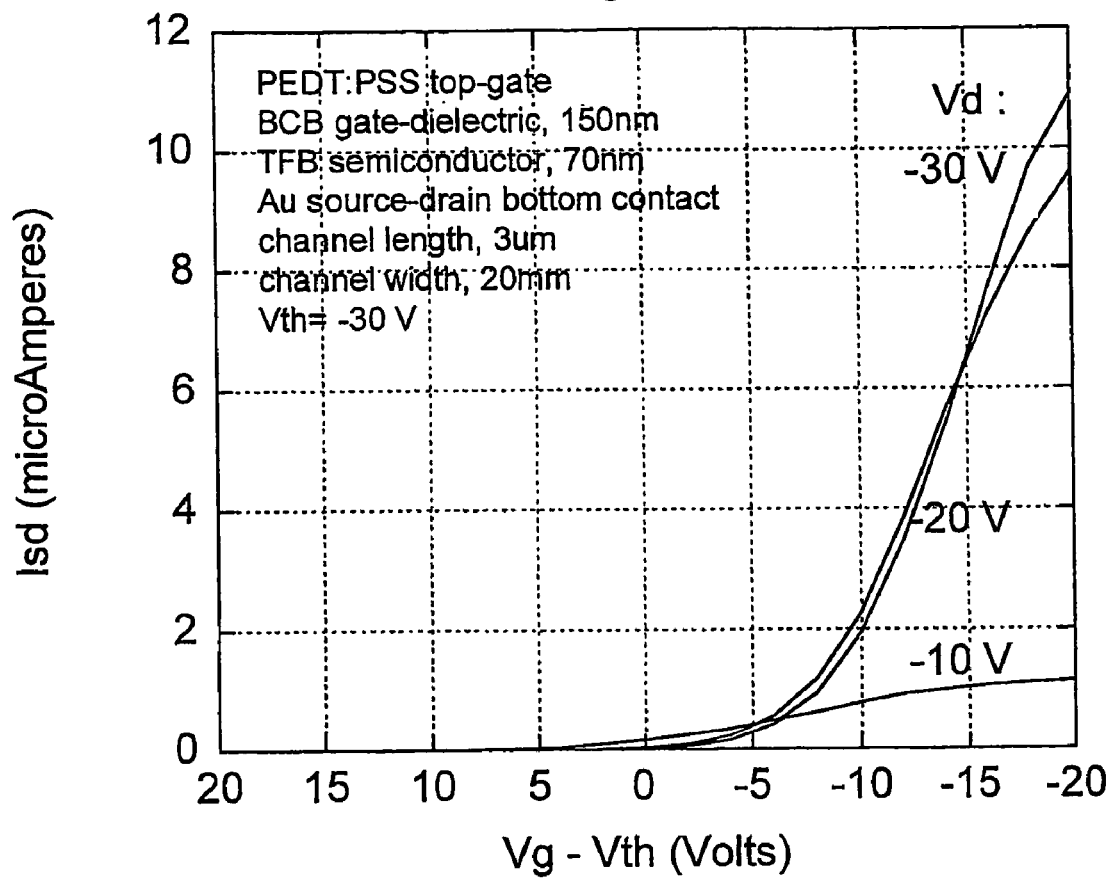
FIG. 4 illustrates the transfer characteristics for a device in accordance with a second embodiment of the invention.
Figure 5:
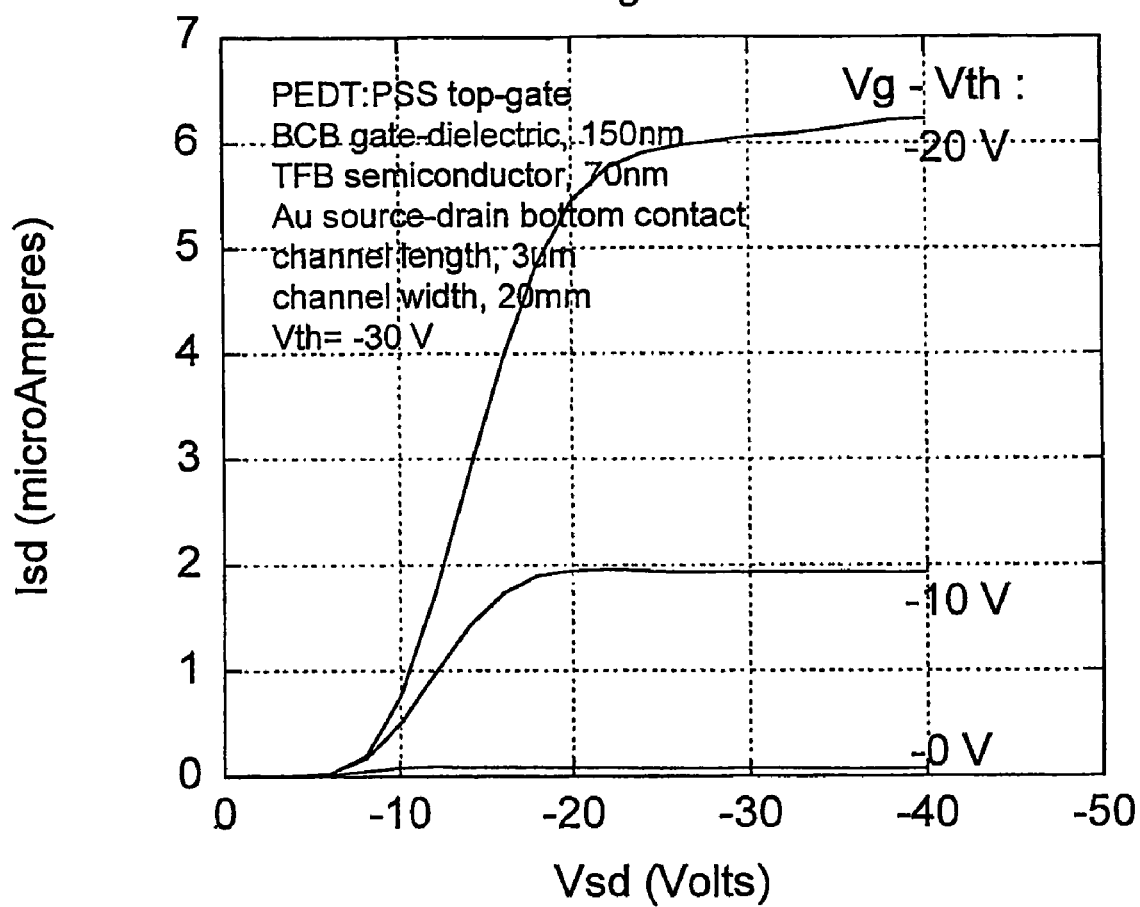
FIG. 5 illustrates the output characteristics for said device in accordance with said second embodiment of the invention.

The transfer characteristics of this 150-nm gate-dielectric device are given in FIG. 4. The threshold gate voltage ($V_{th}$) is ca. 30 volts. This is largely limited by traces of ionic impurities in the TFB semiconductor, as in Example 1. A strong turn-on of the channel conductivity is found when the gate voltage ($V_g$) is increased above this threshold. An "on" source-drain channel current ($I_{sd}$) of few microAmperes is obtained for a drain voltage ($V_d$) of –20 volts, and ($V_g$–$V_{th}$) of –20 volts. On-off ratio is better than 1000. The measured gate current leakage ($I_g$) is less than 5 nA, which is again remarkably small, considering that the electric field strength in the BCB-based polymer gate dielectric at this point is ca. 3 MV/cm. The FET mobility extracted by traditional equations from the $I_{sd}$–$V_g$ slope in the linear regime is near $10^{-3}$ cm$^2$/V s. This is comparable to best values obtained on traditional bottom-gate SiO$_2$/Si gate. The output characteristics are shown in FIG. 5. Good saturation behaviour of $I_{sd}$ is found, indicating that the device is again relatively well behaved.

Example 3

A substrate bearing prepatterned gold source and drain electrodes. The electrodes are 20-nm thick. Channel length is 5 micron. Channel width is 20 mm. The substrate is cleaned by oxygen plasma as described in Example 1. Hexamethyldisilazane is spin onto the substrate at 900 rpm, 30 s, and then the substrate is baked in air on a hotplate for 2 min at 120° C.

TFB (from Cambridge Display Technology, Cambridge, U.K.) at a concentration of 1.8 weight/vol % in mesitylene is blended with a crosslinker at a crosslinker to TFB weight ratio of 1.6% is spun onto the substrate at 1600 rpm, 60 s, to give a 30 nm film. The substrate is then exposed in nitrogen through a photomask to 254-nm radiation for 2 min to crosslink the TFB film, and developed by 10-s mesitylene soak followed by spin-off at 6000 rpm, 30 s.

BCB-based monomer as shown in FIG. 8 in mesitylene (from Dow Chemical Company, MI, U.S.A.) is diluted to a concentration of 12.7 weight/vol % is spin onto the TFB film at 6000 rpm, 60 s, to give a 200 nm film. This gives a d/L ratio of 1/25. (Note, if the TFB film is not crosslinked, application of this BCB-based monomer/mesitylene solution will immediately redissolve the formed TFB layer.) The substrate is then baked under nitrogen on a hotplate for 10 s at 290° C.

PEDT:PSS (from Cambridge Display Technology, Cambridge, U.K.) is applied to give the top-gate electrode as described in Example 1.

Figure 6:
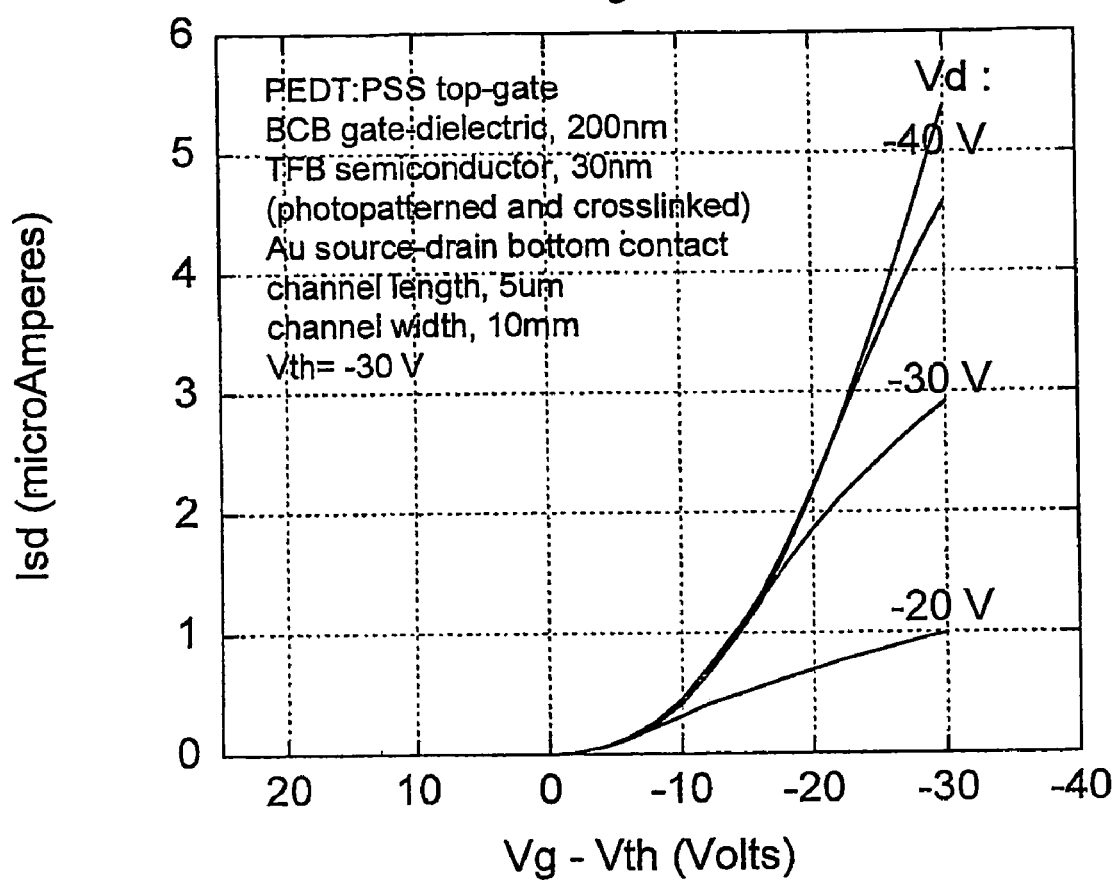
FIG. 6 illustrates the transfer characteristics for a device in accordance with a third embodiment of the invention.
Figure 7:
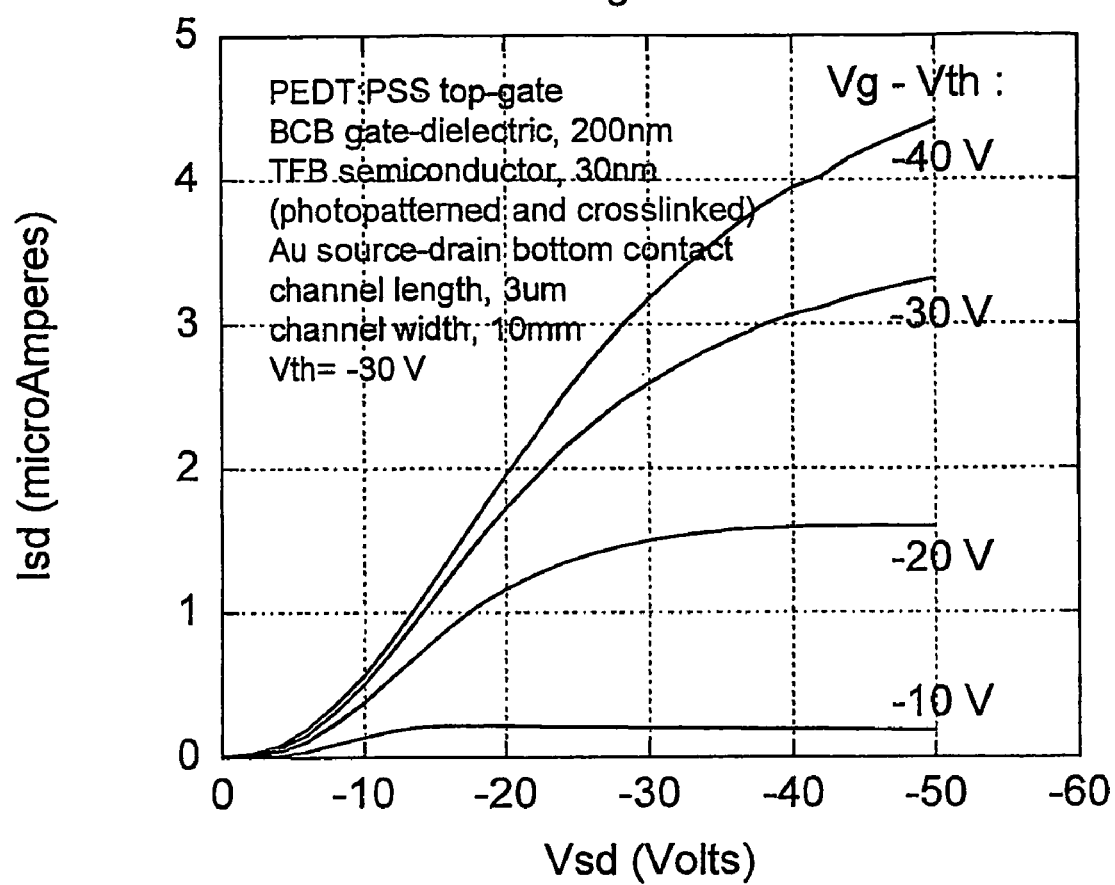
FIG. 7 illustrates the output characteristics for said device in accordance with said third embodiment of the invention.

The transfer characteristics of this 200-nm gate-dielectric device are given in FIG. 6. The threshold gate voltage ($V_{th}$) is ca. –30 volts. This is largely limited by traces of ionic impurities in the TFB semiconductor, as in the other Examples. A strong turn-on of the channel conductivity is found when the gate voltage ($V_g$) is increased above this threshold. An "on" source-drain channel current ($I_{sd}$) of few microAmperes is obtained for a drain voltage ($V_d$) of –20 volts, and ($V_g$–$V_{th}$) of –30 volts. On-off ratio is better than 1000. The measured gate current leakage ($I_g$) is less than 5 nA, which is again remarkably small, considering that the electric field strength in the BCB-based polymer gate dielectric at this point is ca. 3 MV/cm. The FET mobility extracted by traditional equations from the $I_{sd}$–$V_g$ slope in the linear regime is near $4\times10^{-4}$ cm$^2$/V s. The output characteristics are shown in FIG. 7. Good saturation behaviour of $I_{sd}$ is found, indicating that the device is again relatively well behaved.

Example 4

A substrate bearing prepatterned gold source and drain electrodes. The electrodes are 20-nm thick. Channel length is 2 micron. Channel width is 10 mm. The substrate is cleaned by oxygen plasma as described in Example 1. Hexamethyldisilazane is spin onto the substrate at 900 rpm, 30 s, and then the substrate is baked in air on a hotplate for 2 min at 120° C.

TFB (from Cambridge Display Technology, Cambridge, U.K.) at a concentration of 2.1 weight/vol % in mesitylene is blended with a crosslinker at a crosslinker to TFB weight ratio of 1.8% is spun onto the substrate at 1600 rpm, 60 s, to give a 35 nm film. The substrate is then exposed in nitrogen through a photomask to 254-nm radiation for 4 min to crosslink the TFB film, and developed by 10-s soak in mesitylene followed by spin-off at 6000 rpm, 30 s.

BCB-based monomer as shown in FIG. 8 in mesitylene (from Dow Chemical Company, MI, U.S.A.) is diluted to a concentration of 6.4 weight/vol % is spin onto the TFB film at 6000 rpm, 60 s, to give a 50 nm film. This gives a d/L ratio of 1/40. (Note, if the TFB film is not crosslinked, application of this BCB-based monomer/mesitylene solution will immediately redissolve the formed TFB layer.) The substrate is then baked under nitrogen on a hotplate for 10 s at 290° C.

PEDT:PSS (from Cambridge Display Technology, Cambridge, U.K.) is applied to give the top-gate electrode as described in Example 1.

A FET mobility of the order of $10^{-4}$ to $10^{-3}$ cm$^2$/V s is found.

Example 5

A Bottom-gate device is prepared essentially in accordance with each of Examples 1 to 4 where the process steps essentially are reversed.

Example 6

Figure 9:
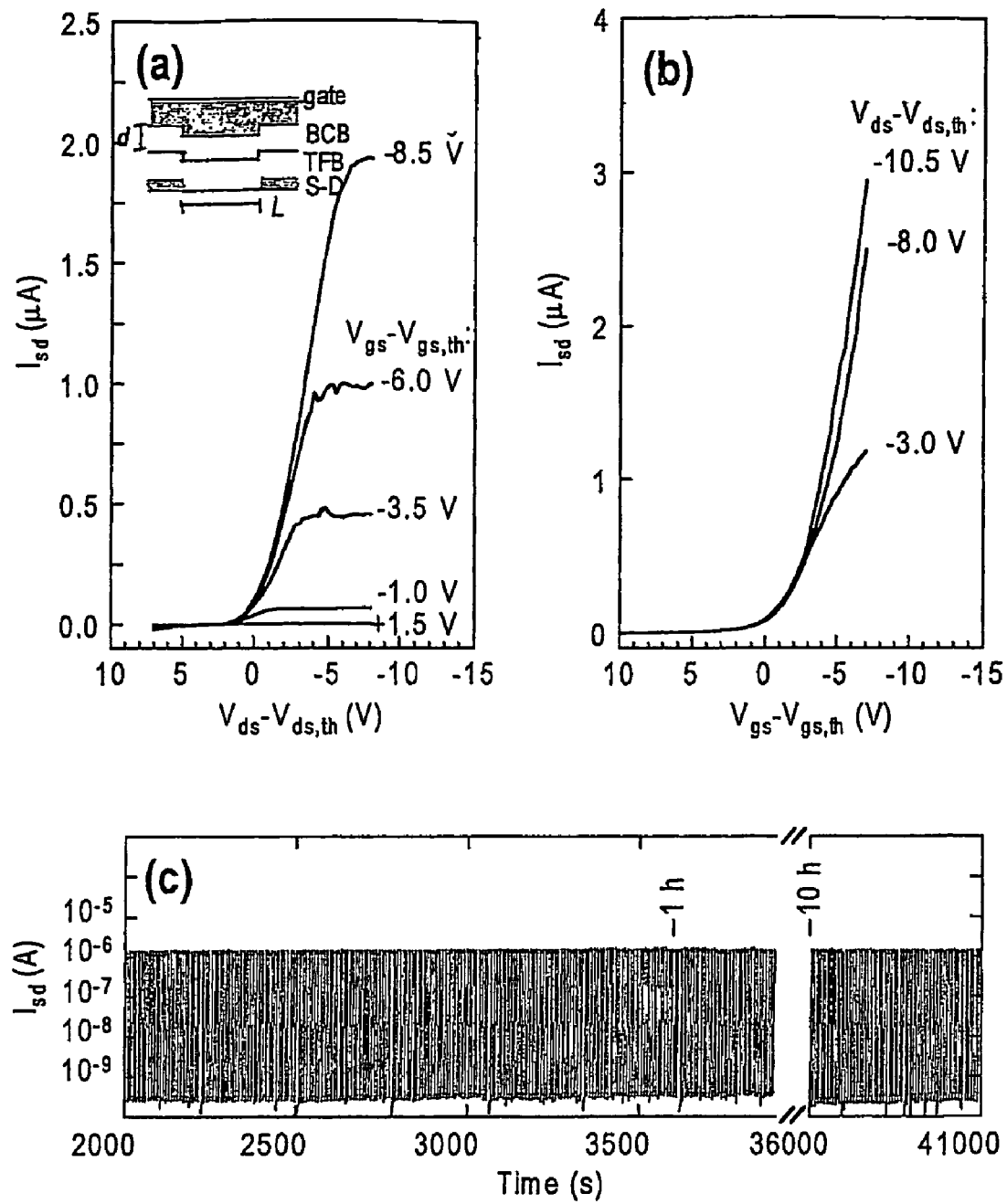
FIG. 9 illustrates the output characteristics, transfer characteristics and stability test results for a device in accordance with a fourth embodiment of the invention.

The schematic structure of the top-gate FET is shown in the inset of FIG. 9. Glass substrates with 15-nm Au source-drain electrodes (3-nm Cr) were treated with hexamethyidisilazane (HMDS), then coated with the p-channel semiconductor (70-nm poly[(9,9-dioctylfluorene-2,7-diyl)alt-(phenylene-(N-(p-2-butylphenyl)imino-phenylene)](TFB) from mesitylene solution), and then the BCB monomer (50-nm from decane solution). [Note: The as-received BGB-mesitylene solution was unsuitable since mesitylene dissolves the underlying TFB layer. BCB monomer was thus extracted on a rotovap and redissolved into decane at 30° C.] The dielectric film was then cured (RTA 290° C., hotplate, 9 s, under N$_2$). The PEDT:PSSR gate electrode was then deposited and annealed in at 80° C. (30 s, air) and then 180° C. (2 min, N$_2$).

Typical output and transfer characteristics are shown in FIGS. 9(a) and (b) respectively. Good saturation behaviour is obtained. There is no significant gate leakage (<10 nA) even at $V_{gs}$=–17.5 V when the gate field is ca. 3 MV/cm. The gate threshold voltage ($V_{gs,th}$) of ca. –9 V is possibly related to ionic impurities in TFB, as evidenced by similar behaviour on separate SiO$_2$/Si bottom-gate devices. The source-drain current ($i_{sd}$) reaches 1 µA at $V_{gs}$=–6 V above threshold with an on-off ratio >$10^4$. There is another threshold ($V_{ds,th}$) arising from contact resistance and the space-charge voltage. The linear-regime field-effect mobility ($\mu_{FET}$) obtained is $3\times10^{-4}$ cm$^2$/Vs, which is comparable to values obtained on bottom-gate FETs with HMDS-treated thermal SiO$_2$ as gate dielectric. This mobility value is limited by the semiconductor itself.

The remarkable stability of this device is shown in FIG. 9(c). It can be cycled at 120° C. between $(V_{gs}-V_{gs,th})=+5$ and $-5$ V with no noticeable degradation of the "on" current or the "on-off" ratio over a 10-h period. This stability is probably related to the high $T_g$ of the crosslinked dielectric (>250° C.) so that it does not dewet the semiconductor surface even for an ultrathin film. Also the results confirm that the interface is free from reactive groups that trap charge carriers.

The invention claimed is:

1. A transistor, comprising:
a semiconductive layer; and
a gate dielectric layer comprising an insulating polymer, wherein, the insulating polymer forms an interface with the semiconductive layer;
the insulating polymer is crosslinked and comprises one or more units having a low cohesive-energy-density and one or more crosslinking groups and the insulating polymer includes substantially no residual —OH leaving groups, and
wherein the semiconductive layer comprises an organic semiconductor.

2. A transistor according to claim 1, wherein the transistor is a field-effect transistor.

3. A transistor according to claim 1, wherein the transistor is a phototransistor.

4. A transistor according to claim 1, wherein the transistor is a chemical sensor.

5. A transistor according to claim 1, wherein the charge-carrier mobility at the semiconductive layer/gate dielectric layer interface is in the range from $10^{-5}$ to $10$ cm$^2$/V s.

6. A transistor according to claim 1, wherein the gate dielectric is thermally stable up to 150° C.

7. A transistor according to claim 1, wherein the insulating polymer has a dielectric breakdown strength of more than 0.5 MV/cm.

8. A transistor according to claim 1, wherein the insulating polymer has a static dielectric constant of at least 2.2.

9. A transistor according to claim 1, wherein the backbone of the insulating polymer comprises one or more low cohesive-energy-density structural units.

10. A transistor according to claim 1, wherein the low cohesive-energy-density structural unit comprises an Si(R)$_2$—O—Si(R)$_2$, Si(R)$_2$—O—Si(R), or Si(R)—O—Si(R) unit where each R independently comprises a hydrocarbon.

11. A transistor according to claim 1, wherein the backbone of the insulating polymer comprises a repeat unit comprising Si(R)$_2$—O—Si(R)$_2$, Si(R)$_2$—O—Si(R), or Si(R)—O—Si(R) where each R independently is methyl or substituted or unsubstituted phenyl.

12. A transistor according to claim 1, wherein the crosslinking group is derivable from a crosslinkable group that can be cured without the loss of a leaving group.

13. A transistor according to claim 12, wherein the insulating polymer comprises a repeat unit having general formula IV:

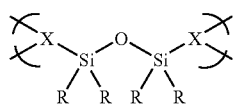

where each X is the same or different and each X represents a crosslinking group and each R independently is a group selected from the group consisting of siloxane, alkyl, aryl, cycloalkyl, alkoxy, and aryloxy groups.

14. A transistor according to claim 13, wherein each crosslinking group comprises 2,3-disubstituted tetrahydronaphthalene.

15. A transistor according to claim 14, wherein the insulating polymer comprises:

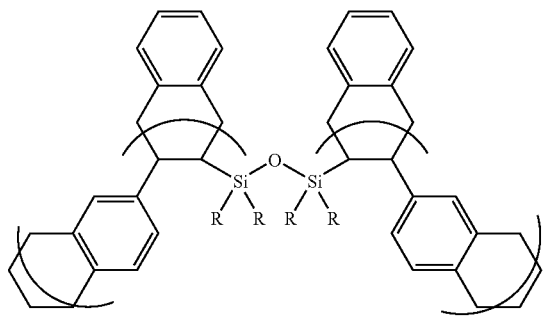

where each R independently is an alkyl group or an aromatic group.

16. A transistor according to claim 12, wherein the insulating polymer comprises a repeat unit having general formula V or VI:

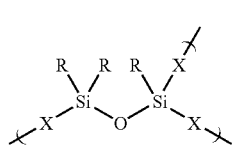

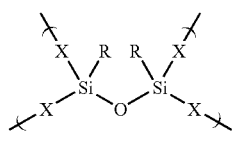

where each X is the same or different and each X represents a crosslinking group and each R independently is a group selected from the group consisting of siloxane, alkyl, aryl, cycloalkyl, alkoxy, and aryloxy groups.

17. A transistor according to claim 16, wherein each X independently comprises a group having general formula XIV:

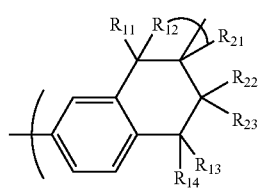

where $R_{11\ to\ 14}$=—H, —CH$_3$; and $R_{21}$ to 23=—H, —CH$_3$.

18. A transistor according to claim 16, wherein each X independently comprises a group having general formula XIX:

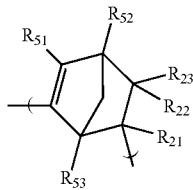

XIX where $R_{51\ to\ 53}$=—H, —CH$_3$; and $R_{21\ to\ 23}$=—H, —CH$_3$.

19. A transistor according to claim 16, wherein each X independently comprises a group having general formula XXIV or XXV:

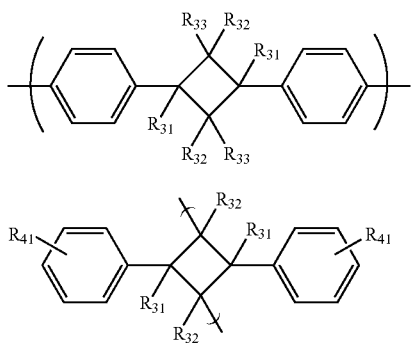

XXIV

XXV where $R_{31\ to\ 33}$=—H, —CH$_3$, or -Ph; and $R_{41}$=alkyl, or aryl.

20. A transistor according to claim 16, wherein each X independently comprises a group having general formula XXVIII:

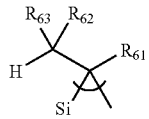

XXVIII where $R_{61\ to\ 63}$=—H, —CH$_3$, or -Ph.

21. A transistor according to claim 1, wherein the thickness of the gate dielectric layer is below 400 nm.

22. A transistor according to claim 21, wherein the operational voltage of the transistor is less than 30 volts.

23. A transistor according to claim 1, wherein the semiconductive layer comprises a semiconductive polymer comprising a fluorene and/or a triarylamine repeat unit.

24. A transistor according to claim 1, wherein the thickness of the semiconductive layer is in the range of 10 nm to 300 nm.

25. An electronic paper, a logic circuit or an RF tag including a transistor according to claim 1.

26. Use in a transistor, comprising a semiconductor layer and a gate dielectric layer forming an interface with the semiconductor layer, of (1) a crosslinked polymer comprising one or more units having a low cohesive-energy-density and one or more crosslinking groups and substantially not including any residual —OH leaving groups, as a gate dielectric for the gate dielectric layer forming an interface with the semiconductor layer, and (2) an organic semiconductor as the semiconductor layer.

27. The transistor as recited in claim 1 wherein the semiconductor layer comprises a polymer.

28. The use in a transistor of a crosslinked polymer as recited in claim 26, wherein the semiconductor layer comprises a polymer.

\* \* \* \* \*